United States Patent [19]
Al-Razzak et al.

[11] Patent Number: 5,948,436
[45] Date of Patent: *Sep. 7, 1999

[54] PHARMACEUTICAL COMPOSITION

[75] Inventors: Laman A. Al-Razzak, Libertyville; Kennan C. Marsh, Lake Forest; Dilip Kaul, Waukegan; Lourdes P. Manning, Grayslake, all of Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/402,690

[22] Filed: Mar. 13, 1995

Related U.S. Application Data

[63] Continuation-in-part of application No. 08/288,873, Aug. 15, 1994, abandoned, which is a continuation-in-part of application No. 08/267,331, Jun. 28, 1994, abandoned, which is a continuation-in-part of application No. 08/188,511, Jan. 28, 1994, abandoned, which is a continuation-in-part of application No. 08/120,886, Sep. 13, 1993, abandoned.

[51] Int. Cl.$^6$ ...................................................... A61K 9/48
[52] U.S. Cl. ........................... 424/456; 424/455; 424/489; 514/212; 514/255; 514/231.2; 514/307; 514/365; 514/491
[58] Field of Search ..................................... 424/451, 456, 424/455, 489; 514/212, 255, 231.2, 307, 365, 491

[56] References Cited

U.S. PATENT DOCUMENTS

| | | | |
|---|---|---|---|
| 5,206,219 | 4/1993 | Desai | 514/3 |
| 5,354,866 | 10/1994 | Kempf et al. | 546/265 |
| 5,484,801 | 1/1996 | Al-Razzak et al. | 514/365 |
| 5,541,206 | 7/1996 | Kempf et al. | 514/365 |
| 5,725,878 | 3/1998 | Al-Razzak et al. | 424/456 |

FOREIGN PATENT DOCUMENTS

| | | |
|---|---|---|
| 486948 | 5/1992 | European Pat. Off. . |
| 490667 | 6/1992 | European Pat. Off. . |
| 532466 | 3/1993 | European Pat. Off. . |
| 541168 | 5/1993 | European Pat. Off. . |
| WO92/08701 | 5/1992 | WIPO . |
| WO92/15319 | 9/1992 | WIPO . |
| WO93/07128 | 4/1993 | WIPO . |
| WO94/05639 | 3/1994 | WIPO . |
| WO94/14436 | 7/1994 | WIPO . |

OTHER PUBLICATIONS

Mimoto, et al., Chem. Pharm. Bull. 40(8) 2251–2253 (1992).

*Primary Examiner*—Jyothsna Venkat
*Attorney, Agent, or Firm*—Steven R. Crowley

[57] ABSTRACT

A pharmaceutical composition is disclosed which comprises a solution of an HIV protease inhibiting compound in a pharmaceutically acceptable organic solvent comprising a pharmaceutically acceptable alcohol. The composition can optionally comprise a pharmaceutically acceptable acid or a combination of pharmaceutically acceptable acids. The solution can optionally be encapsulated in hard gelatin capsules or soft elastic gelatin capsules. The solution can optionally be granulated with a pharmaceutically acceptable granulating agent.

44 Claims, No Drawings

PHARMACEUTICAL COMPOSITION

This is a continuation-in-part of U.S. patent application Ser. No. 288,873, filed Aug. 15, 1994 now abandonded, which is a continuation-in-part of U.S. patent application Ser. No. 267,331, filed Jun. 28, 1994 now abandonded, which is a continuation-in-part of U.S. patent application Ser. No. 188,511, filed Jan. 28, 1994 now abandonded, which is a continuation-in-part of U.S. patent application Ser. No. 120,886, filed Sep. 13, 1993 now abandonded.

TECHNICAL FIELD

A liquid, semi-solid or solid pharmaceutical composition providing improved oral bioavailability is disclosed for compounds which are inhibitors of HIV protease (in particular, HIV-1 and HIV-2 protease). In particular, the composition comprises a solution of the HIV protease inhibitor in a pharmaceutically acceptable organic solvent or a mixture of pharmaceutically acceptable organic solvents, the solvent comprising a pharmaceutically acceptable alcohol. The composition can optionally be granulated by mixing with a pharmaceutically acceptable granulating agent or mixture of granulating agents. The composition can optionally be encapsulated in either hard gelatin capsules or soft elastic capsules (SEC).

BACKGROUND OF THE INVENTION

One measure of the potential usefulness of an oral dosage form of a new pharmaceutical agent is the bioavailability observed after oral administration of the dosage form. Various factors can affect the bioavailability of a drug when administered orally. These factors include aqueous solubility, drug absorption throughout the gastrointestinal tract, dosage strength and first pass effect. Aqueous solubility is one of the most important of these factors. When a drug has poor aqueous solubility, attempts are often made to identify salts or other derivatives of the drug which have improved aqueous solubility. When a salt or other derivative of the drug is identified which has good aqueous solubility, it is generally accepted that an aqueous solution formulation of this salt or derivative will provide the optimum oral bioavailability. The bioavailability of the aqueous oral solution formulation of a drug is then generally used as the standard or ideal bioavailability against which other oral dosage forms are measured.

For a variety of reasons, such as patient compliance and taste masking, a solid dosage form, such as capsules, is usually preferred over a liquid dosage form. However, oral solid dosage forms of a drug generally provide a lower bioavailability than oral solutions of the drug. One goal of the development of a suitable capsule dosage form is to obtain a bioavailability of the drug that is as close as possible to the ideal bioavailability demonstrated by the oral aqueous solution formulation of the drug.

It has recently been determined that HIV protease inhibiting compounds are useful for inhibiting HIV protease in vitro and in vivo, are useful for inhibiting HIV (human immunodeficiency virus) infections and are useful for treating AIDS (acquired immunodeficiency syndrome). HIV protease inhibiting compounds typically are characterized by having poor oral bioavailability.

Examples of HIV protease inhibiting compounds include N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide and related compounds, disclosed in European Patent Application No. EP541168, published May 12, 1993, which is incorporated herein by reference; N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide (i.e., saquinavir) and related compounds, disclosed in U.S. Pat. No. 5,196,438, issued Mar. 23, 1993, which is incorporated herein by reference; 5(S)-Boc-amino-4(S)-hydroxy-6-phenyl-2(R)-phenylmethylhexanoyl-(L)-Val-(L)-Phe-morpholin-4-ylamide and related compounds, disclosed in European Patent Application No. EP532466, published Mar. 17, 1993, which is incorporated herein by reference;

1-Naphthoxyacetyl-beta-methylthio-Ala-(2S,3S)-3-amino-2-hydroxy-4-butanoyl-1,3-thiazolidine-4-t-butylamide (i.e., 1-Naphthoxyacetyl-Mta-(2S,3S)-AHPBA-Thz-NH-tBu), 5-isoquinolinoxyacetyl-beta-methylthio-Ala-(2S,3S)-3-amino-2-hydroxy-4-butanoyl-1,3-thiazolidine-4-t-butylamide (i.e., iQoa-Mta-Apns-Thz-NHtBu) and related compounds, disclosed in European Patent Application No. EP490667, published Jun. 17, 1992 and Chem. Pharm. Bull. 40 (8) 2251 (1992), which are incorporated herein by reference;

[1S-[1R*(R*),2S*]]-N¹[3-[[[(1,1-dimethylethyl)amino]carbonyl](2-methylpropyl)amino]-2-hydroxy-1-(phenylmethyl)propyl]-2-[(2-quinolinylcarbonyl)amino]-butanediamide and related compounds, disclosed in PCT Patent Application No. WO92/08701, published May 29, 1992, which is incorporated herein by reference;

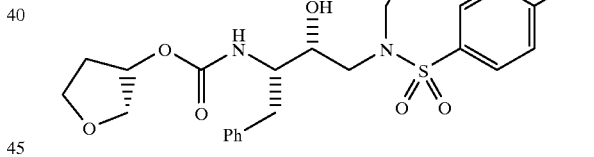

and related compounds, disclosed in PCT Patent Application No. WO94/05639, published Mar. 17, 1994, which is incorporated herein by reference;

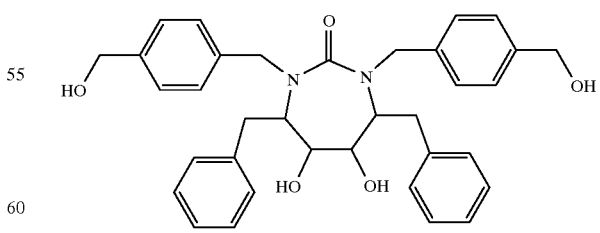

and related compounds, disclosed in PCT Patent Application No. WO93/07128, published Apr. 15, 1993, which is incorporated herein by reference; and AG1343, i.e.,

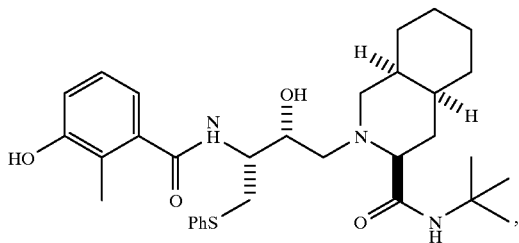

disclosed in 13th Int. Symp. Med. Chem. (Paris) 1994, Abst. ML8, which is incorporated herein by reference.

It has recently been determined that compounds of the formula I:

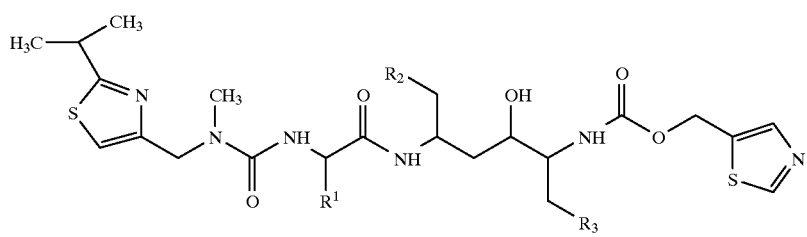

wherein $R_1$ is lower alkyl and $R_2$ and $R_3$ are phenyl are inhibitors of HIV-1 and HIV-2 protease and are useful to inhibit HIV infections and, thus, are useful for the treatment of AIDS.

In particular, the compound of formula II, has been found to be especially effective as an inhibitor of HIV-1 and HIV-2 protease.

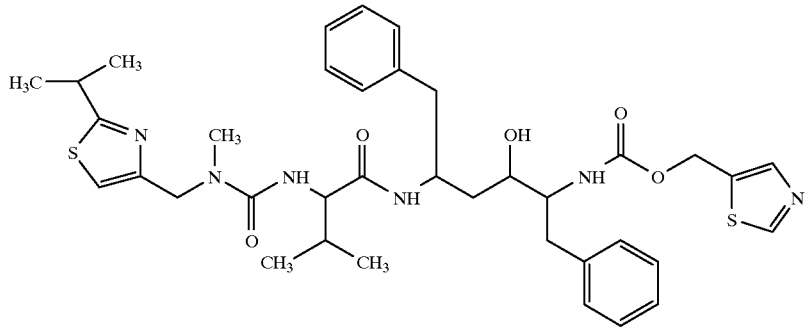

The most preferred compound of formula II is (2S,3S, 5S)-5-(N-(N-((N-Methyl-N-((2-isopropyl-4-thiazolyl) methyl)-amino)carbonyl)valinyl)amino)-2-(N-((5-thiazolyl) methoxycarbonyl)amino)-1,6-diphenyl-3-hydroxyhexane (compound III).

Compound III has an aqueous solubility of approximately 6 micrograms per milliliter at pH >2. This is considered to be extremely poor aqueous solubility and, therefore, compound III in the free base form would be expected to provide very low oral bioavailability. In fact, the free base form of compound III, administered as an unformulated solid in a capsule dosage form, is characterized by a bioavailability of less than 2% following a 5 mg/kg oral dose in dogs.

Acid addition salts of compound III (for example, bis-hydrochloride, bis-tosylate, bis-methane sulfonate and the like) have aqueous solubilities of <0.1 milligrams/milliliter. This is only a slight improvement over the solubility of the free base. This low aqueous solubility would not make practical the administration of therapeutic amounts of an acid addition salt of compound III as an aqueous solution. Furthermore, in view of this low aqueous solubility, it is not surprising that the bis-tosylate of compound III, administered as an unformulated solid in a capsule dosage form, is characterized by a bioavailability of less than 2% following a 5 mg/kg oral dose in dogs.

In order to have a suitable oral dosage form of compound III, the oral bioavailability of compound III should be at least 20%. Preferably, the oral bioavailability of compound III from the dosage form should be greater than about 40% and, more preferably, greater than about 50%.

While some drugs would be expected to have good solubility in organic solvents, it would not necessarily follow that oral administration of such a solution would give good bioavailability for the drug. It has been found that compound III has good solubility in pharmaceutically acceptable organic solvents and that the solubility in such solvents is enhanced by at least four times in the presence of a pharmaceutically acceptable acid. Unexpectedly, these solutions of compound III in organic solvents provide an oral bioavailability of from about 20% to about 40% in dogs. Quite unexpectedly, administration of the solution as an encapsulated dosage form (soft elastic capsules or hard gelatin capsules) provides an oral bioavailability of as high as about 90% or more. In addition, quite unexpectedly, when certain solution compositions of compound III are granulated by mixing with a pharmaceutically acceptable granulating agent and the resulting solid composition is administered to dogs, an acceptable oral bioavailabitlity is observed.

DISCLOSURE OF THE INVENTION

In accordance with the present invention, there is a pharmaceutical composition comprising a solution of an HIV protease inhibiting compound (preferably, a compound of the formula II) in a pharmaceutically acceptable organic solvent or a mixture of pharmaceutically acceptable organic solvents, the solvent comprising a pharmaceutically acceptable alcohol.

Also in accordance with the present invention, there is a pharmaceutical composition comprising a solution of an HIV protease inhibiting compound (preferably, a compound of the formula II) in a pharmaceutically acceptable organic solvent or a mixture of pharmaceutically acceptable organic solvents, the solvent comprising a pharmaceutically acceptable alcohol, wherein the solution is encapsulated in a soft elastic gelatin capsule (SEC) or a hard gelatin capsule.

The solution composition of the invention can also comprise from about 0 to about 3 molar equivalents (based on the amount of the HIV protease inhibiting compound in the composition) of a pharmaceutically acceptable acid or a mixture of pharmaceutically acceptable acids. Preferably, the pharmaceutically acceptable acid or mixture of pharmaceutically acceptable acids is present in a total amount of from about 0.2 to about 2.0 molar equivalents (based on the amount of the HIV protease inhibiting compound in the composition).

The solution composition of the invention can also comprise from about 0% to about 10% (by weight of the total solution) of water. In addition, the solution composition of the invention can comprise a pharmaceutically acceptable surfactant or a mixture of pharmaceutically acceptable surfactants. In addition, the solution composition of the invention can comprise an antioxidant (for example, ascorbic acid, BHA (butylated hydroxyanisole), BHT (butylated hydroxytoluene), vitamin E, vitamin E PEG 1000 succinate and the like) for chemical stability. Solutions encapsulated in a SEC may also comprise glycerin for physical stability.

The compositions of this invention (solution or encapsulated solution) provide improved oral bioavailability for compound II when compared to non-formulated compound II (base) or non-formulated compound II (acid addition salt), or even when compared to a mixed aqueous/organic solution (50% water, 20% ethanol, 30% propylene glycol) of compound II (methansulfonate acid addition salt).

The term "pharmaceutically acceptable organic solvent" as used herein refers to polypropylene glycol; polyethylene glycol (for example, polyethylene glycol 600, polyethylene glycol 900, polyethylene glycol 540, polyethylene glycol 1450, polyethylene glycol 6000, polyethylene glycol 8000 (all available from Union Carbide) and the like); pharmaceutically acceptable alcohols which are liquids at about room temperature, approximately 20° C., (for example, propylene glycol, ethanol, 2-(2-ethoxyethoxy)ethanol (Transcutol®, Gattefosse, Westwood, N.J. 07675), benzyl alcohol, glycerol, polyethylene glycol 200, polyethylene glycol 300, polyethylene glycol 400 and the like); polyoxyethylene castor oil derivatives (for example, polyoxyethyleneglyceroltriricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.) and the like); saturated polyglycolized glycerides (for example, Gelucire® 35/10, Gelucire® 44/14, Gelucire® 46/07, Gelucire® 50/13 or Gelucire® 53/10 and the like, available from Gattefosse, Westwood, N.J. 07675); polyoxyethylene alkyl ethers (for example, cetomacrogol 1000 and the like); polyoxyethylene stearates (for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, PEG-150 distearate and the like); ethyl oleate, isopropyl palmitate, isopropyl myristate and the like; dimethyl isosorbide; N-methylpyrrolidinone; parafin; cholesterol; lecithin; suppository bases; pharmaceutically acceptable waxes (for example, carnauba wax, yellow wax, white wax, microcrystalline wax, emulsifying wax and the like); pharmaceutically acceptable silicon fluids; soribitan fatty acid esters (including sorbitan laurate, sorbitan oleate, sorbitan palmitate, sorbitan stearate and the like); pharmaceutically acceptable saturated fats or pharmaceutically acceptable saturated oils (for example, hydrogenated castor oil (glyceryl-tris-12-hydroxystearate), cetyl esters wax (a mixture of primarily C14–C18 saturated esters of C14–C18 saturated fatty acids having a melting range of about 43–47° C.), glyceryl monostearate and the like); and the like.

Pharmaceutically acceptable solvents also include pharmaceutically acceptable oils such as mineral oil or a vegetable oil (for example, safflower oil, peanut oil, olive oil, fractionated coconut oil (for example, mixed triglycerides with caprylic acid and capric acid (Miglyol® 812, available from Huls AG, Witten, Germany) and the like), propyleneglycol monolaurate and the like.

Saturated polyglycolized glycerides are described in the French Pharmacopeia 10th Edition. In particular, saturated polyglycolized glycerides are mixtures of mono-, di- and tri-glycerides and polyethylene glycol mono- and di-esters obtained either by partial alcoholysis of hydrogenated vegetable oils using polyethylene glycol of relative molecular weight ranging from 200–2000, or by esterification of saturated fatty acids using polyethylene glycol of relative molecular weight ranging from 200–2000 and glycerol. Each saturated polyglycolized glyceride is characterized by its nominal drop point, its nominal hydroxyl and saponification values and its nominal composition in fatty acids. The free glycerol content is less than 1%.

More particularly, the preferred saturated polyglycolized glycerides are characterized as follows.

Gelucire® 35/10
drop point: 29–34° C. (preferably, 31.2° C.)
hydroxyl value: 70–90 mg KOH/g (preferably, 74 mg KOH/g)
saponification value: 120–134 mg KOH/g (preferably, 134 mg KOH/g)
fatty acid composition:
caprylic acid (C8): 1–7% (preferably, 2.1%)
capric acid (C10): 1–7% (preferably, 2.2%)
lauric acid (C12): 31–41% (preferably, 35.4%)
myristic acid (C14): 7–17% (preferably, 12.9%)
palmitic acid (C16): 12–22% (preferably, 20.7%)
stearic acid (C18): 23–33% (preferably, 26.2%)

Gelucire® 44/14
drop point: 42.5–47.5° C.
hydroxyl value: 30–50 mg KOH/g
saponification value: 76–90 mg KOH/g
fatty acid composition:
caprylic acid (C8): 4–10%
capric acid (C10): 3–9%
lauric acid (C12): 40–50%
myristic acid (C14): 14–24%
palmitic acid (C16): 4–14%
stearic acid (C18): 5–15%

Gelucire® 46/07 drop point: 47–52° C. (preferably, 49.3° C.)
hydroxyl value: 65–85 mg KOH/g (preferably, 70 mg KOH/g)
saponification value: 126–140 mg KOH/g (preferably, 139 mg KOH/g)
fatty acid composition:
caprylic acid (C8): <3% (preferably, <0.1%)
capric acid (C10): <3% (preferably, <0.1%)
lauric acid (C12): <5% (preferably, 0.9%)
myristic acid (C14): <5% (preferably, 1.4%)
palmitic acid (C16): 40–50% (preferably, 44%)
stearic acid (C18): 48–58% (preferably, 52.8%)
Gelucire® 50/13
drop point: 46–51° C. (preferably, 48.7° C.)
hydroxyl value: 36–56 mg KOH/g (preferably, 52 mg KOH/g)
saponification value: 67–81 mg KOH/g (preferably, 74 mg KOH/g)
fatty acid composition:
caprylic acid (C8): <3% (preferably, 0.2%)
capric acid (C10): <3% (preferably, 0.2%)
lauric acid (C12): <5% (preferably, 2.2%)
myristic acid (C14): <5% (preferably, 1.8%)
palmitic acid (C16): 40–50% (preferably, 42.5%)
stearic acid (C18): 48–58% (preferably, 52.6%)
Gelucire® 53/10
drop point: 49–54° C. (preferably, 52.5° C.)
hydroxyl value: 25–45 mg KOH/g (preferably, 35 mg KOH/g)
saponification value: 98–112 mg KOH/g (preferably, 104 mg KOH/g)
fatty acid composition:
caprylic acid (C8): <3% (preferably, <0.1%)
capric acid (C10): <3% (preferably, <0.1%)
lauric acid (C12): <5% (preferably, 0.4%)
myristic acid (C14): <5% (preferably, 1.0%)
palmitic acid (C16): 40–50% (preferably, 43%)
stearic acid (C18): 48–58% (preferably, 54.2%)

The term "pharmaceutically acceptable acid" as used herein refers to (i) an inorganic acid such as hydrochloric acid, hydrobromic acid, hydroiodic acid and the like, (ii) an organic mono-, di- or tri-carboxylic acid (for example, formic acid, acetic acid, adipic acid, alginic acid, citric acid, ascorbic acid, aspartic acid, benzoic acid, butyric acid, camphoric acid, gluconic acid, glucuronic acid, galactaronic acid, glutamic acid, heptanoic acid, hexanoic acid, fumaric acid, lactic acid, lactobionic acid, malonic acid, maleic acid, nicotinic acid, oxalic acid, pamoic acid, pectinic acid, 3-phenylpropionic acid, picric acid, pivalic acid, propionic acid, succinic acid, tartaric acid, undecanoic acid and the like) or (iii) a sulfonic acid (for example, benzenesulfonic acid, sodium bisulfate, sulfuric acid, camphorsulfonic acid, dodecylsulfonic acid, ethanesulfonic acid, methanesulfonic acid, isethionic acid, naphthalenesulfonic acid, p-toluenesulfonic acid and the like).

The term "pharmaceutically acceptable surfactant" as used herein refers to a pharmaceutically acceptable non-ionic surfactant (for example, polyoxyethylenepolypropylene glycol, such as Poloxamer®68 (BASF Wyandotte Corp.) or a mono fatty acid ester of polyoxyethylene (20) sorbitan (for example, polyoxyethylene (20) sorbitan monooleate (Tween® 80), polyoxyethylene (20) sorbitan monostearate (Tween® 60), polyoxyethylene (20) sorbitan monopalmitate (Tween® 40), polyoxyethylene (20) sorbitan monolaurate (Tween® 20) and the like) and the like) or a soribitan fatty acid ester (including sorbitan laurate, sorbitan oleate, sorbitan palmitate, sorbitan stearate and the like) or a pharmaceutically acceptable anionic surfactant (for example, sodium lauryl sulfate and the like).

The term "solution" as used herein refers to solutions of the pharmaceutically active agent dissolved in the pharmaceutically acceptable solvent or mixture of solvents wherein the solution remains in liquid form at about room temperature; or it refers to semi-solid solutions wherein the pharmaceutically active agent is dissolved in a pharmaceutically acceptable solvent or mixture of solvents which is a liquid at temperatures above about room temperature (particularly, at about the temperature of the human body) but is a solid or semi-solid at about room temperature.

A preferred composition of the invention comprises a solution of (1) an HIV protease inhibiting compound (preferably, a compound of the formula II); and (2) a pharmaceutically acceptable acid or a mixture of pharmaceutically acceptable acids in a pharmaceutically acceptable organic solvent or a mixture of pharmaceutically acceptable organic solvents, the solvent comprising a pharmaceutically acceptable alcohol.

Another preferred composition of the invention comprises a solution of (1) a compound of the formula II in the amount of from about 2% to about 30% (preferably, from about 4% to about 30%) by weight of the total solution; and (2) a total of from about 0.2 molar equivalent to about 3 molar equivalents (based on compound II) of (i) a pharmaceutically acceptable acid or (ii) a mixture of pharmaceutically acceptable acids in a pharmaceutically acceptable organic solvent or a mixture of pharmaceutically acceptable organic solvents, the solvent comprising a pharmaceutically acceptable alcohol.

Yet another preferred composition of the invention comprises a solution of (1) an HIV protease inhibiting compound (preferably, a compound of the formula II); and (2) a pharmaceutically acceptable acid or a mixture of pharmaceutically acceptable acids in a pharmaceutically acceptable organic solvent or a mixture of pharmaceutically acceptable organic solvents, the solvent comprising a pharmaceutically acceptable alcohol, wherein the solution is encapsulated in a soft elastic gelatin capsule (SEC) or a hard gelatin capsule.

Yet another preferred composition of the invention comprises a solution of (1) a compound of the formula II in the amount of from about 2% to about 30% (preferably, from about 4% to about 30%) by weight of the total solution; and (2) a total of from about 0.2 molar equivalent to about 3 molar equivalents (based on compound II) of (i) a pharmaceutically acceptable acid or (ii) a mixture of pharmaceutically acceptable acids in a pharmaceutically acceptable organic solvent or a mixture of pharmaceutically acceptable organic solvents, the solvent comprising a pharmaceutically acceptable alcohol, wherein the solution is encapsulated in a soft elastic gelatin capsule (SEC) or a hard gelatin capsule.

Preferably, the pharmaceutically acceptable organic solvent or mixture of pharmaceutically acceptable organic solvents comprises from about 50% to about 95% by weight of the total solution. More preferably, the pharmaceutically acceptable organic solvent or mixture of pharmaceutically acceptable organic solvents comprises from about 70% to about 95% by weight of the total solution.

Preferred pharmaceutically acceptable alcohols include propylene glycol, polyethylene glycol, ethanol and benzyl alcohol.

Preferred pharmaceutically acceptable solvents comprise (1) propylene glycol or a mixture of propylene glycol (about 80% v/v) and ethanol (about 20% v/v) or (2) a mixture of propylene glycol (from about 80% to about 90% v/v), ethanol (from about 5% to about 10% v/v) and water (from about 5% to about 10% v/v) or (3) a mixture of propylene glycol (from about 5% to about 40% by weight of the total solution) and ethanol (from about 2% to about 20% by weight of the total solution).

Other preferred pharmaceutically acceptable solvents comprise (i) polyethylene glycol (most preferably, polyethylene glycol 540, polyethylene glycol 900, polyethylene glycol 600 or polyethylene glycol 400) or (ii) a mixture of polyethylene glycols (for example, polyethylene glycol 900 (about 40% by weight of the total solution) and polyethylene glycol 300 (about 40% by weight of the total solution)) or (iii) a mixture of polyethylene glycol (about 80% by weight of the total solution) and propylene glycol (from about 5% to about 12% by weight of the total solution) or (iv) a mixture of polyethylene glycol (about 70% by weight of the total solution), propylene glycol (about 4% by weight of the total solution) and ethanol (about 4% by weight of the total solution), (v) a mixture of polyethylene glycol and a polyoxyethylene castor oil derivative (for example, a mixture of polyethylene glycol 600 (about 32% by weight of the total solution) and polyoxyethyleneglycerol triricinoleate (about 42% by weight of the total solution)), (vi) a mixture of propylene glycol (from about 20% to about 25% by weight of the total solution), ethanol (from about 5% to about 10% by weight of the total solution) and a saturated polyglycolized glyceride (in particular, Gelucire® 44/14 or Gelucire® 50/13 (from about 30% to about 35% by weight of the total solution), (vii) a mixture of propylene glycol (from about 10% to about 15% by weight of the total solution), ethanol (from about 5% to about 10% by weight of the total solution) and a saturated polyglycolized glyceride (in particular, Gelucire® 44/14 or Gelucire® 50/13 (from about 30% to about 35% by weight of the total solution) or (viii) a mixture of propylene glycol (from about 4% to about 10% by weight of the total solution), ethanol (from about 10% to about 20% by weight of the total solution), benzyl alcohol (from about 3% to about 10% by weight of the total solution) and a saturated polyglycolized glyceride (in particular, Gelucire® 50/13 (from about 25% to about 40% by weight of the total solution).

A preferred pharmaceutically acceptable acid is hydrochloric acid, citric acid, p-toluenesulfonic acid or sulfuric acid or a mixture of two of these acids.

A more preferred composition of the invention comprises a solution of: (1) a compound of the formula II in the amount of from about 2% to about 30% (preferably, from about 4% to about 30%) by weight of the total solution; and (2) a total of from about 0.2 to about 2 molar equivalents (based on compound II) of (i) a pharmaceutically acceptable acid or (ii) a mixture of pharmaceutically acceptable acids in a pharmaceutically acceptable organic solvent or a mixture of pharmaceutically acceptable organic solvents, the solvent comprising a pharmaceutically acceptable alcohol, wherein the solution is encapsulated in a soft elastic capsule or a hard gelatin capsule.

In the more preferred composition of the invention, the preferred pharmaceutically acceptable solvents and acids are as described above for the preferred composition of the invention.

A most preferred composition of the invention comprises a solution of (1) a compound of the formula III in the amount of from about 2% to about 30% (preferably, from about 4% to about 30%) by weight of the total solution; and (2) a total of from about 0.2 to about 2 molar equivalents (based on compound III) of (i) a pharmaceutically acceptable acid or (ii) a mixture of pharmaceutically acceptable acids in a pharmaceutically acceptable organic solvent or a mixture of pharmaceutically acceptable organic solvents, the solvent comprising a pharmaceutically acceptable alcohol, wherein the solution is encapsulated in a soft elastic capsule or a hard gelatin capsule.

In the most preferred composition of the invention, the preferred pharmaceutically acceptable solvents and acids are as described above for the preferred composition of the invention.

An even more preferred composition of the invention comprises a solution of (1) an HIV protease inhibiting compound (especially, a compound of the formula III) in the amount of from about 2% to about 30% by weight of the total solution (preferably, from about 15% to about 25% by weight of the total solution) and (2) a total of from about 0.2 to about 2 molar equivalents (based on compound III) of (i) a pharmaceutically acceptable acid or (ii) a mixture of pharmaceutically acceptable acids in a pharmaceutically acceptable organic solvent comprising a mixture of (a) a pharmaceutically acceptable alcohol or mixture of pharmaceutically acceptable alcohols in a total amount of from about 2% to about 50% by weight of the total solution, said alcohol or mixture of alcohols being a liquid at room temperature and (b) a pharmaceutically acceptable organic solvent or a mixture of pharmaceutically acceptable organic solvents in a total amount of from about 20% to about 60% by weight of the total solution, said solvent or mixture of solvents having a melting point between about 20° C. and about 60° C. (preferably, between about 20° C. and about 50° C.), said solvent or mixture of solvents being miscible with the alcohol or mixture of alcohols and providing a homogeneous mixture with the alcohol or mixture of alcohols, said homogeneous mixture being a solid or semi-solid at about 20° C., wherein the solution is encapsulated in a soft elastic capsule or a hard gelatin capsule.

An even more preferred composition of the invention comprises a solution of (1) an HIV protease inhibiting compound (especially, a compound of the formula III) in the amount of from about 2% to about 30% by weight of the total solution (preferably, from about 15% to about 25% by weight of the total solution) and (2) a total of from about 0.2 to about 2 molar equivalents (based on compound III) of (i) a pharmaceutically acceptable acid or (ii) a mixture of pharmaceutically acceptable acids in a pharmaceutically acceptable organic solvent comprising a mixture of (a) propylene glycol in the amount of from about 4% to about 40% by weight of the total solution, (b) ethanol in the amount of from about 2% to about 20% (preferably, from about 5% to about 20% by weight of the total solution and, more preferably, from about 7% to about 18% by weight of the total solution), and (c) polyethylene glycol 540 in the amount of from about 20% to about 60% (preferably, from about 30% to about 40% by weight of the total solution) or a total amount of from about 20% to about 60% by weight of the total solution (preferably, from about 25% to about 40% by weight of the total solution and, more preferably, from about 30% to about 40% by weight of the total solution) of (i) a saturated polyglycolized glyceride ((in particular, Gelucire® 35/10, Gelucire® 44/14, Gelucire® 46/07, Gelucire® 50/13 or Gelucire® 53/10 and the like) or (ii) a mixture of saturated polyglycolized glycerides, wherein the solution is encapsulated in a soft elastic capsule or a hard gelatin capsule.

In the even more preferred composition of the invention, if the composition comprises from about 2% to about 20% by weight of the total solution of compound III, it is not necessary for the composition to comprise a pharmaceutically acceptable acid.

A most highly preferred composition of the invention comprises a solution of (1) a compound of the formula III in the amount of from about 20% to about 25% by weight of the total solution and (2) a total of from about 1.5 to about 2 molar equivalents (based on compound III) of hydrochloric acid in a pharmaceutically acceptable organic solvent comprising a mixture of (a) propylene glycol in the amount of from about 20% to about 22% by weight of the total solution, (b) ethanol in the amount of from about 5% to about 6% by weight of the total solution, and (c) saturated polyglycolized glyceride (in particular, Gelucire® 44/14 or Gelucire® 35/10) in the amount of from about 30% to about 35% by weight of the total solution, wherein the solution is encapsulated in a hard gelatin capsule.

Another most highly preferred composition of the invention comprises a solution of (1) a compound of the formula III in the amount of from about 15% to about 20% by weight of the total solution and (2) a total of from about 0.3 to about 0.6 molar equivalents (based on compound III) of hydrochloric acid in a pharmaceutically acceptable organic solvent comprising a mixture of (a) propylene glycol in the amount of about 12% by weight of the total solution, (b) ethanol in the amount of from about 5% to about 6% by weight of the total solution, and (c) saturated polyglycolized glyceride (in particular, Gelucire® 44/14 or Gelucire® 50/13) in the amount of from about 30% to about 35% by weight of the total solution, wherein the solution is encapsulated in a hard gelatin capsule.

Another most highly preferred composition of the invention comprises a solution of (1) a compound of the formula III in the amount of from about 15% to about 20% by weight of the total solution and (2) a total of from about 0.3 to about 0.6 molar equivalents (based on compound III) of hydrochloric acid in a pharmaceutically acceptable organic solvent comprising a mixture of (a) propylene glycol in the amount of about 12% by weight of the total solution, (b) ethanol in the amount of from about 10% to about 15% by weight of the total solution, and (c) saturated polyglycolized glyceride (in particular, Gelucire® 44/14 or Gelucire® 50/13) in the amount of from about 30% to about 35% by weight of the total solution, wherein the solution is encapsulated in a hard gelatin capsule.

Another most highly preferred composition of the invention comprises a solution of (1) a compound of the formula III in the amount of from about 10% to about 15% by weight of the total solution and (2) a total of from about 0.3 to about 0.6 molar equivalents (based on compound III) of hydrochloric acid in a pharmaceutically acceptable organic solvent comprising a mixture of (a) propylene glycol in the amount of about 15% by weight of the total solution, (b) ethanol in the amount of from about 10% to about 15% by weight of the total solution, and (c) saturated polyglycolized glyceride (in particular, Gelucire® 44/14 or Gelucire® 50/13) in the amount of from about 30% to about 35% by weight of the total solution, wherein the solution is encapsulated in a hard gelatin capsule.

Another most highly preferred composition of the invention comprises a solution of (1) a compound of the formula III in the amount of from about 15% to about 20% by weight of the total solution and (2) a total of from about 0.3 to about 0.8 molar equivalents (based on compound III) of hydrochloric acid in a pharmaceutically acceptable organic solvent comprising a mixture of (a) propylene glycol in the amount of from about 13% to about 14% by weight of the total solution, (b) ethanol in the amount of about 14% by weight of the total solution, and (c) saturated polyglycolized glyceride (in particular, Gelucire® 44/14 or Gelucire® 50/13) in the amount of from about 30% to about 35% by weight of the total solution, wherein the solution is encapsulated in a hard gelatin capsule.

Another most highly preferred composition of the invention comprises a solution of (1) a compound of the formula III in the amount of from about 15% to about 20% by weight of the total solution in a pharmaceutically acceptable organic solvent comprising a mixture of (a) propylene glycol in the amount of about 40% by weight of the total solution, (b) ethanol in the amount of about 2% to about 3% by weight of the total solution, and (c) polyethylene glycol 540 in the amount of from about 30% to about 35% by weight of the total solution, wherein the solution is encapsulated in a hard gelatin capsule.

Another most highly preferred composition of the invention comprises a solution of (1) a compound of the formula III in the amount of from about 10% to about 15% by weight of the total solution and (2) a total of from about 1.10 to about 1.30 molar equivalents (based on compound III) of citric acid in a pharmaceutically acceptable organic solvent comprising a mixture of (a) propylene glycol in the amount of from about 5% to about 7% by weight of the total solution, (b) ethanol in the amount of about 15% to about 20% by weight of the total solution, and (c) saturated polyglycolized glyceride (in particular, Gelucire® 50/13) in the amount of from about 30% to about 35% by weight of the total solution, wherein the solution is encapsulated in a hard gelatin capsule.

Another most highly preferred composition of the invention comprises a solution of (1) a compound of the formula III in the amount of from about 10% to about 15% by weight of the total solution and (2) a total of from about 0.8 to about 0.9 molar equivalents (based on compound III) of citric acid in a pharmaceutically acceptable organic solvent comprising a mixture of (a) propylene glycol in the amount of from about 5% to about 7% by weight of the total solution, (b) ethanol in the amount of about 10% to about 15% by weight of the total solution, (c) benzyl alcohol in the amount of from about 3% to about 4% by weight of the total solution, and (d) saturated polyglycolized glyceride (in particular, Gelucire® 50/13) in the amount of from about 35% to about 40% by weight of the total solution, wherein the solution is encapsulated in a hard gelatin capsule.

Another most highly preferred composition of the invention comprises a solution of (1) a compound of the formula III in the amount of about 20% by weight of the total solution and (2) a total of from about 0.7 to about 0.8 molar equivalents (based on compound III) of citric acid in a pharmaceutically acceptable organic solvent comprising a mixture of (a) propylene glycol in the amount of from about 4% to about 6% by weight of the total solution, (b) ethanol in the amount of about 10% to about 15% by weight of the total solution, (c) benzyl alcohol in the amount of from about 4% to about 6% by weight of the total solution, and (d) saturated polyglycolized glyceride (in particular, Gelucire® 50/13) in the amount of from about 30% to about 35% by weight of the total solution, wherein the solution is encapsulated in a hard gelatin capsule.

Another most highly preferred composition of the invention comprises a solution of (1) a compound of the formula III in the amount of about 25% by weight of the total solution and (2) a mixture of a total of from about 0.4 to about 0.5 molar equivalents (based on compound III) of citric acid and a total of from about 0.10 to about 0.25 molar equivalents (based on compound III) of sulfuric acid in a pharmaceutically acceptable organic solvent comprising a mixture of (a) propylene glycol in the amount of from about 5% to about 7% by weight of the total solution, (b) ethanol in the amount of about 10% to about 15% by weight of the total solution, (c) benzyl alcohol in the amount of from about 4% to about 6% by weight of the total solution, and (d) saturated polyglycolized glyceride (in particular, Gelucire® 50/13) in the amount of from about 25% to about 30% by weight of the total solution, wherein the solution is encapsulated in a hard gelatin capsule.

Another most highly preferred composition of the invention comprises a solution of (1) a compound of the formula III in the amount of about 25% by weight of the total solution and (2) a total of from about 0.7 to about 0.8 molar equivalents (based on compound III) of citric acid in a pharmaceutically acceptable organic solvent comprising a mixture of (a) propylene glycol in the amount of from about 4% to about 6% by weight of the total solution, (b) ethanol in the amount of about 15% to about 20% by weight of the total solution, (c) benzyl alcohol in the amount of from about 5% to about 10% by weight of the total solution, and (d) saturated polyglycolized glyceride (in particular, Gelucire® 50/13) in the amount of from about 25% to about 30% by weight of the total solution, wherein the solution is encapsulated in a hard gelatin capsule.

Another embodiment of the present invention comprises a solid pharmaceutical composition comprising a mixture of (A) a solution of (1) an HIV protease inhibiting compound (preferably, a compound of the formula III) in the amount of from about 4% to about 30% by weight of the total solution (preferably, from about 15% to about 25% by weight of the total solution) and (2) a total of from about 0.2 to about 2 molar equivalents (based on the HIV protease inhibiting compound) of (i) a pharmaceutically acceptable acid or (ii) a mixture of pharmaceutically acceptable acids in a pharmaceutically acceptable organic solvent comprising a mixture of (a) a pharmaceutically acceptable alcohol or mixture of pharmaceutically acceptable alcohols in a total amount of from about 2% to about 50% by weight of the total solution, said alcohol or mixture of alcohols being a liquid at about room temperature and (b) a pharmaceutically acceptable solvent or a mixture of pharmaceutically acceptable solvents in a total amount of from about 20% to about 60% by weight of the total solution, said solvent or mixture of solvents having a melting point between about 20° C. and about 60° C. (preferably, between about 20° C. and about 50° C.), said solvent or mixture of solvents being miscible with the alcohol or mixture of alcohols and providing a homogeneous mixture with the alcohol or mixture of alcohols, said homogeneous mixture being a solid or semi-solid at about 20° C. and (B) a pharmaceutically acceptable granulating agent or a mixture of pharmaceutically acceptable granulating agents. A more preferred embodiment comprises the above-mentioned solid composition as a granulation which is encapsulated in a hard gelatin capsule for administration.

An even more preferred embodiment of the solid composition comprises a solid pharmaceutical composition comprising a mixture of (A) a solution of (1) a compound of the formula III in the amount of from about 4% to about 30% by weight of the total solution (preferably, from about 15% to about 25% by weight of the total solution) and (2) a total of from about 0.2 to about 2 molar equivalents (based on compound III) of (i) a pharmaceutically acceptable acid or (ii) a mixture of pharmaceutically acceptable acids in a pharmaceutically acceptable organic solvent comprising a mixture of (a) propylene glycol in the amount of from about 5% to about 40% by weight of the total solution, (b) ethanol in the amount of from about 2% to about 20% (preferably, from about 2% to about 8% by weight of the total solution and, more preferably, from about 5% to about 6% by weight of the total solution), and (c) polyethylene glycol 540 in the amount of from about 20% to about 60% (preferably, from about 30% to about 40% by weight of the total solution) or a total amount of from about 20% to about 60% by weight of the total solution (preferably, from about 25% to about 40% by weight of the total solution and, more preferably, from about 30% to about 40% by weight of the total solution) of (i) a saturated polyglycolized glyceride ((in particular, Gelucire® 35/10, Gelucire® 44/14, Gelucire® 46/07, Gelucire® 50/13 or Gelucire® 53/10 and the like) or (ii) a mixture of saturated polyglycolized glycerides and (B) a pharmaceutically acceptable granulating agent or a mixture of pharmaceutically acceptable granulating agents. A most preferred embodiment comprises the above-mentioned solid composition as a granulation which is encapsulated in a hard gelatin capsule for administration.

The term "pharmaceutically acceptable granulating agent" as used herein refers to silicon dioxide, colloidal silicon dioxide (for example, Cab-o-sil®, available from Cabot Corp.), microcrystalline cellulose, starch, talc, calcium carbonate, pectin, aluminum silicate, maltodextrin, crospovidone (for example, Polyplasdone®XL or XL10, available from GAF Corp.) and the like.

Preferably, the pharmaceutically acceptable granulating agent or mixture of pharmaceutically acceptable granulating agents comprises from about 0.5% to about 30% by weight of the solid pharmaceutical composition.

The compounds of formula I and II contain two or more asymmetric carbon atoms and thus can exist as pure diastereomers, mixtures of diastereomers, diastereomeric racemates or mixtures of diastereomeric racemates. The present invention is intended to include within its scope all of the isomeric forms. The terms "R" and "S" configuration as used herein are as defined by IUPAC 1974 Recommendations for Section E, Fundamental Stereochemistry, Pure Appl. Chem. (1976) 45, 13–30.

The preferred isomer of the compound of formula II is (2S,3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane (compound III).

The term "lower alkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The composition and preparation of the soft elastic gelatin capsule itself is well known in the art. The composition of a soft elastic gelatin capsule typically comprises from about 30% to about 50% by weight of gelatin NF, from about 20% to about 30% by weight of a plasticizer and from about 25% to about 40% by weight of water. Plasticizers useful in the preparation of soft elastic gelatin capsules are glycerin, sorbitol or propylene glycol and the like; or combinations thereof. A preferred soft elastic gelatin capsule has a composition comprising gelatin NF (Type 195) (about 42.6% by weight), glycerin (USP) (about 96% active; about 13.2% by weight), purified water (USP) (about 27.4% by weight), sorbitol special (about 16% by weight) and titanium dioxide (USP) (about 0.4% by weight).

The soft elastic gelatin capsule material can also comprise additives such as preservatives, opacifiers, dyes or flavors and the like.

Various methods can be used for manufacturing and filling the soft elastic gelatin capsules, for example, a seamless capsule method, a rotary method (developed by Scherer) or a method using a Liner machine or an Accogel machine and the like. Also various manufacturing machines can be used for manufacturing the capsules.

Hard gelatin capsules are purchased from Capsugel, Greenwood, S.C. Capsules are filled manually or by capsule filling machine. The target filling volume/weight depends on the potency of the filling solution in combination with the desired dosage strength.

In general, the compositions of this invention can be prepared in the following manner. The pharmaceutically acceptable organic solvent or mixture of solvents is mixed with any additives (for example, water, pharmaceutically acceptable oils, glycerin, pharmaceutically acceptable surfactants or antioxidants). To this mixture is added the pharmaceutically acceptable acid with stirring. To this mixture is added the HIV protease inhibiting compound (for example, the compound of formula II) with stirring. Additional solvent is added until a clear solution is obtained and/or to reach the desired final volume of solution. The appropriate volume of final solution needed to provide the desired dose of the HIV protease inhibiting compound can be filled into hard gelatin capsules or soft elastic gelatin capsules.

In general, the even more preferred compositions of the invention can be prepared in the following manner. The pharmaceutically acceptable alcohol (other than ethanol) is mixed with any other additives such as surfactants. If ethanol is part of composition, the ethanol is added to this solution and stirred until the solution is clear to slightly cloudy. The pharmaceutically acceptable acid or mixture of acids is added and the solution is stirred until it is clear to slightly cloudy. The HIV protease inhibiting compound (for example, compound II) is added and the solution is stirred until it is clear or slightly cloudy. The other pharmaceutically acceptable solvent or mixture of solvents (for example, polyethylene glycol or saturated polyglycolized glyceride) is heated just enough to be liquified. The liquified solvent is added to the alcohol solution of the HIV protease inhibiting compound with mixing (with appropriate temperature control to maintain the mixture as solution, but without causing degradation of the HIV protease inhibiting compound). The appropriate volume of final solution needed to provide the desired dose of the HIV protease inhibiting compound can be filled into hard gelatin capsules or soft elastic gelatin capsules.

In general, the solid pharmaceutical composition of the invention can be prepared in the following manner. The pharmaceutically acceptable liquid alcoholic solvent(s) (other than ethanol) is mixed with any other additives, such as surfactants. If ethanol is one of the solvents, the ethanol is then added to the above mixture and stirred until the solution is clear to slightly cloudy. Then the pharmaceutically acceptable acid (or mixture of acids) is added and the mixture is stirred until it is clear to slightly cloudy. The HIV protease inhibiting compound (for example, compound II) is added and the mixture is stirred until it is clear to slightly cloudy. The other pharmaceutically acceptable solvent or mixture of solvents (for example, polyethylene glycol or saturated polyglycolized glyceride) is heated just enough to be liquified. The liquified solvent is added to the solution of the HIV protease inhibiting compound and stirred well. This solution is added slowly with mixing to the granulating agent and mixed well until the mixture is a dry solid. The resulting solid is passed through an appropriately sized seive to obtain granules. The appropriate amount of the granulation to provide the desired dose is filled into hard gelatin capsules.

The following examples will serve to further illustrate the invention.

EXAMPLE 1 (non-formulated capsule)

An amount of compound III (free base) equivalent to a 5 mg/kg dose was placed in hard gelatin capsules (gray, size 0). These capsules were administered to fasted dogs with 10 ml of water.

EXAMPLE 2 (Capsule)

An amount of compound III (free base) equivalent to a 5 mg/kg dose was placed in hard gelatin capsules (gray, size 0). These capsules were administered to non-fasted dogs with ten milliliter of water.

EXAMPLE 3 (Capsule)

An amount of the bis-tosylate salt of compound III equivalent to a 5 mg/kg dose of compound III (base equivalent) was filled into hard gelatin capsules (gray, size 0). These capsules were administered to fed dogs with ten milliliter of water.

EXAMPLE 4 (Solution)

A 5 mg (free base equivalent)/ml solution of the base compound III in 20% ethanol: 30% propylene glycol: dextrose containing 2-molar equivalents of methane sulfonic acid.

| Component | % By Weight |
|---|---|
| Compound III (free base) | 0.5 |
| Propylene glycol (Aldrich, reagent) | 31.9 |
| Ethanol (USP, 200 proof) | 16.2 |
| methanesulfonic acid (Aldrich reagent) | 0.14 |
| Dextrose | 3.6 |
| Water for injection (USP) | 47.6 |

EXAMPLE 5 (SEC)

A 100 mg/ml solution of the base compound III in 20% ethanol: 80% polyethylene glycol-400 encapsulated in SEC.

| Component | % By Weight |
|---|---|
| Compound III (free base) | 8.6 |
| Polyethylene glycol 400 (USP) | 77.8 |
| Ethanol (USP, 200 proof) | 13.5 |

EXAMPLE 6 (SEC)

A 100 mg/ml solution of the base compound III in 20% ethanol: 80% propylene glycol with 50 mg/ml p-toluene sulfonic acid, encapsulated in SEC.

| Component | % By Weight |
|---|---|
| Compound III (free base) | 8.8 |
| Propylene glycol (NF) | 73.0 |
| Ethanol (USP, 200 proof) | 13.8 |
| p-toluenesulfonic acid (Sigma, reagent) | 4.4 |

EXAMPLE 7 (SEC)

A 100 mg/ml solution of the base compound III in 20% ethanol: 80% propylene glycol encapsulated in SEC.

| Component | % By Weight |
|---|---|
| Compound III (free base) | 9.2 |
| Propylene glycol 400 (NF) | 76.3 |
| Ethanol (USP, 200 proof) | 14.5 |

EXAMPLE 8 (SEC)

A 100 mg/ml solution of the base compound III in 98% propylene glycol, 2% glycerin with 50.0 mg/ml p-toluene sulfonic acid encapsulated in SEC.

| Component | % By Weight |
|---|---|
| Compound III (free base) | 8.4 |
| Propylene glycol (NF) | 85.6 |
| Glycerin (USP, 96%) | 1.38 |
| p-toluenesulfonic acid (Sigma, reagent) | 4.2 |

EXAMPLE 9 (capsule)

| Component | % By Weight |
|---|---|
| Compound III (free base) | 10.0 |
| Polyethylene Glycol 540 | 74.5 |
| Propylene glycol | 10.0 |
| p-toluene sulfonic acid, monohydrate, Sigma | 5.5 |

EXAMPLE 10 (solution)

A 45 mg/ml solution of the base compound III in 9% ethanol, 9% water, 82% propylene glycol with 24.0 mg/ml p-toluene sulfonic acid and 45 mg/ml aspartame.

| Component | % By Weight |
|---|---|
| Compound III (free base) | 4.0 |
| Propylene glycol (NF) | 75.5 |
| Ethanol (USP, 200 proof) | 6.3 |
| p-toluenesulfonic acid (Sigma, reagent) | 2.1 |
| Water for injection (USP) | 8.0 |
| Aspartame | 4.0 |

EXAMPLE 11 (capsule)

| Component | % By Weight |
|---|---|
| Compound III (free base) | 17.0 |
| Polyethylene Glycol 540 | 68.1 |
| Propylene glycol | 4.3 |
| Ethanol | 4.3 |
| Glycerin | 1.7 |
| p-toluene sulfonic acid, monohydrate, Sigma | 4.7 |

EXAMPLE 12 (capsule)

| Component | % By Weight |
|---|---|
| Compound III (free base) | 10.0 |
| Polyethylene Glycol 540 | 80.0 |
| Propylene glycol | 5.0 |
| p-toluene sulfonic acid, monohydrate, Sigma | 5.1 |

EXAMPLE 13 (capsule)

| Component | % By Weight |
|---|---|
| Compound III (free base) | 5.0 |
| Polyethylene Glycol 300 | 80.0 |
| Propylene glycol | 12.3 |
| p-toluene sulfonic acid, monohydrate, Sigma | 2.8 |

EXAMPLE 14 (capsule)

| Component | % By Weight |
|---|---|
| Compound III (free base) | 10.0 |
| Polyethylene Glycol 900 | 42.3 |
| Polyethylene Glycol 300 | 42.2 |
| p-toluene sulfonic acid, monohydrate, Sigma | 5.5 |

EXAMPLE 15 (capsule)

| Component | % By Weight |
|---|---|
| Compound III (free base) | 10.0 |
| Polyethylene Glycol 540 | 84.5 |
| p-toluene sulfonic acid, monohydrate, Sigma | 5.5 |

EXAMPLE 16 (capsule)

| Component | % By Weight |
|---|---|
| Compound III (free base) | 12.5 |
| Polyethylene Glycol 540 | 80.6 |
| p-toluene sulfonic acid, monohydrate, Sigma | 6.9 |

EXAMPLE 17 (capsule)

A 100 mg/ml solution of the base compound III in 90% propylene glycol, 5% ethanol, 5% water with 2 molar equivalents of hydrochloric acid encapsulated in hard gelatin capsule.

| Component | % By Weight |
|---|---|
| Compound III (free base) | 8.8 |
| Propylene glycol (NF) | 82.3 |
| Ethanol (USP, 200 proof) | 3.5 |
| Hydrochloric acid (reagent) | 0.9 |
| Water for injection (USP) | 4.4 |

To propylene glycol (700 mL) was added ethanol (50 mL, 200 proof) with stirring. Water for injection (13.7 mL) was added with stirring, followed by the addition with stirring of hydrochloric acid (46.7 mL, 554.8 mmol). To this mixture was added compound III (200 g, 277.4 mmol). Stirring was continued until a clear solution was obtained. Propylene glycol was then added to give a total volume of one liter. The appropriate volume of this solution was filled into hard gelatin capsules.

EXAMPLE 18 (capsule)

| Component | % By Weight |
|---|---|
| Compound III (free base) | 21.0 |
| Polyethylene Glycol 600 | 31.6 |
| Hydrochloric acid, reagent | 5.3 |
| Cremophor ® EL | 42.1 |

EXAMPLE 19 (SEC)

| Component | % By Weight |
|---|---|
| Compound III (free base) | 20.1 |
| Polyethylene glycol 600 (USP) | 68.4 |
| Hydrochloric acid (reagent) | 4.6 |
| Water for injection (USP) | 1.6 |
| Ascorbic acid (USP) | 1.25 |
| Gylcerin (USP, 96%) | 4.0 |

In an appropriately sized container, was mixed 36.8 mL of concentrated hydrochloric acid, water for injection (12.5 mL), glycerin (32 g), ascorbic acid (10 g) and polyethylene glycol 600 (540 mL). The mixture was stirred until a homogeneous solution was obtained. To this solution was slowly added compound III (160 g, 221 mmol) with continuous stirring until a clear solution was obtained. This solution was transferred to an appropriate container and the head space was purged with nitrogen. The appropriate volume of this solution was filled into soft elastic gleatin capsules.

EXAMPLE 20 (SEC)

| Component | % By Weight |
|---|---|
| Compound III (free base) | 16.0 |
| Propylene Glycol (NF) | 10.0 |
| Citric acid (anhydrous) | 16.0 |
| Cremophor ® EL | 33.0 |
| Ethanol (USP, 200 proof) | 5.0 |
| Tween ® 80 (USP) | 20.0 |

Propylene glycol (1.0 g) and citric acid (1.6 g) were mixed with stirring. To this mixture was added Tween® 80 (2.0 g) with stirring. Compound III (1.6 g, 2.22 mmol) was added, making a thick white paste. To this mixture was added ethanol (0.5 g) and Cremophore® EL (3.3 g). After mixing well, a clear solution was obtained. Sonication was used to help remove trapped air bubbles from the solution. The appropriate volume of this solution was filled into soft elastic gelatin capsules.

EXAMPLE 21 (capsule)

| Component | % By Weight |
|---|---|
| Compound III (free base) | 2.0 |
| Propylene Glycol (NF) | 2.64 |
| Ethanol (USP, 200 proof) | 5.36 |
| Polyethylene glycol 540 | 90.0 |

EXAMPLE 22 (capsule)

| Component | % By Weight |
|---|---|
| Compound III (free base) | 22.12 |
| Propylene Glycol (NF) | 29.5 |
| p-toluenesulfonic acid, monohydrate, Sigma | 5.8 |
| Cremophor ® RH40 | 3.7 |
| Ethanol (USP, 200 proof) | 5.50 |
| Polyethylene glycol 540 | 33.3 |

EXAMPLE 23 (capsule)

| Component | % By Weight |
|---|---|
| Compound III (free base) | 22.12 |
| Propylene Glycol (NF) | 29.5 |
| p-toluenesulfonic acid, monohydrate, Sigma | 5.8 |
| Cremophor ® RH40 | 3.7 |
| Ethanol (USP, 200 proof) | 5.50 |
| Gelucire ® 44/14 | 33.3 |

EXAMPLE 24 (capsule)

| Component | % By Weight |
|---|---|
| Compound III (free base) | 15.01 |
| Propylene Glycol (NF) | 40.06 |
| p-toluenesulfonic acid, monohydrate, Sigma | 3.97 |
| Tween ® 80 | 5.05 |
| Ethanol (USP, 200 proof) | 2.52 |
| Polyethylene glycol 540 | 33.4 |

Propylene glycol and polysorbate 80 were mixed until the solution was clear to slightly cloudy. Ethanol was added and the solution was stirred until the solution was clear or slightly cloudy. p-Toluenesulfonic acid was added to the solution and stirred until the solution was clear or slightly cloudy. Compound III was added to the solution and stirred until the solution was clear or slightly cloudy. Polyethylene glycol 540 was heated to not more than 45° C. until it was in the liquid state. The heated polyethylene glycol 540 was then added to the solution of compound III and the mixture was stirred well. The appropriate volume of this final mixture to provide the desired dose of compound III was filled into hard gelatin capsules.

EXAMPLE 25 (capsule)

| Component | % By Weight |
|---|---|
| Compound III (free base) | 21.95 |
| Propylene Glycol (NF) | 25.64 |
| hydrochloric acid, reagent | 5.85 |
| Cremophor ® RH40 | 3.76 |
| Ethanol (USP, 200 proof) | 5.48 |
| Gelucire ® 44/14 | 33.3 |
| Miglyol ®812 | 3.98 |

EXAMPLE 26 (capsule)

| Component | % By weight |
| --- | --- |
| Compound III (free base) | 22.1 |
| Propylene Glycol (NF) | 25.75 |
| hydrochloric acid, reagent | 5.9 |
| Ethanol (USP, 200 proof) | 5.56 |
| Gelucire ® 44/14 | 33.29 |
| Miglyol ® 812 | 3.73 |
| Tween ® 80 | 3.66 |

EXAMPLE 27 (capsule)

| Component | % By weight |
| --- | --- |
| Compound III (free base) | 21.78 |
| Propylene Glycol (NF) | 19.91 |
| Hydrochloric acid, reagent | 5.96 |
| Cremophor ® RH40 | 6.82 |
| Ethanol (USP, 200 proof) | 5.51 |
| Gelucire ® 44/14 | 33.28 |
| Miglyol ® 812 | 6.73 |

EXAMPLE 28 (capsule)

| Component | % By Weight |
| --- | --- |
| Compound III (free base) | 18.03 |
| Propylene Glycol (NF) | 12.36 |
| Citric acid (USP, anhydrous, powder) | 4.12 |
| Hydrochloric acid, reagent | 1.83 |
| Cremophor ® EL | 17.51 |
| Ethanol (USP, 200 proof) | 5.10 |
| Tween ® 80 (USP) | 5.10 |
| Gelucire ® 44/14 | 33.38 |
| Miglyol ® | 2.58 |

EXAMPLE 29 (SEC)

| Component | % By Weight |
| --- | --- |
| Compound III (free base) | 16.0 |
| Propylene glycol (USP) | 10.0 |
| Ethanol (USP, 200 proof, dehydrated) | 5.0 |
| Cremophor ® EL (polyoxyl 35, castor oil, NF) | 33.0 |
| Citric acid (USP, anhydrous, powder) | 16.0 |
| Tween ® 80 | 20.0 |

EXAMPLE 30 (capsule)

| Component | % By Weight |
| --- | --- |
| Compound III (free base) | 14.99 |
| Propylene Glycol (NF) | 40.03 |
| Hydrochloric acid, reagent | 4.50 |
| Tween ® 80 | 5.10 |
| Ethanol (USP, 200 proof) | 2.55 |
| Polyethylene glycol 540 | 32.83 |

Propylene glycol and Tween® 80 (USP) were mixed until the solution was clear to slightly cloudy. Ethanol was added and the solution was stirred until the solution was clear or slightly cloudy. Hydrochloric acid was added to the solution and stirred until the solution was clear or slightly cloudy. Compound III was added to the solution and stirred until the solution was clear or slightly cloudy. Polyethylene glycol 540 was heated to not more than 45° C. until it was in the liquid state. The heated polyethylene glycol 540 was then added to the solution of compound III and the mixture was stirred well. The appropriate volume of this final mixture to provide the desired dose of compound III was filled into hard gelatin capsules.

EXAMPLE 31 (capsule)

| Component | % By Weight |
| --- | --- |
| Compound III (free base) | 22.12 |
| Propylene Glycol (NF) | 29.5 |
| p-toluenesulfonic acid, monohydrate, Sigma | 5.8 |
| Cremophor ® RH40 | 3.7 |
| Ethanol (USP, 200 proof) | 5.5 |
| Polyethylene glycol 540 | 33.3 |

Step 1. The compound of formula III was dissolved in the ethanol with mixing. The propylene glycol was added and mixing was continued until a homogeneous solution was obtained. All of the remaining ingredients (except the acid and the polyethylene glycol) were added and mixing was continued until a homogeneous solution was obtained. The acid was then added with mixing.

Step 2. The polyethylene glycol was warmed (to not more than 45° C.) until it was liquified. The liquified polyethylene glycol was then added with mixing to the solution resulting from Step 1. The appropriate volume of this final mixture to provide the desired dose of compound III was filled into hard gelatin capsules.

EXAMPLE 32 (capsule)

| Component | % By Weight |
| --- | --- |
| Compound III (free base) | 22.12 |
| Propylene Glycol (NF) | 29.5 |
| p-toluenesulfonic acid, monohydrate, Sigma | 5.8 |
| Cremophor ® RH40 | 3.7 |
| Ethanol (USP, 200 proof) | 5.5 |
| Gelucire ® 44/14 | 33.3 |

This composition was prepared according to the process of Example 31 with the exception that the polyethylene glycol was replaced by Gelucire® 44/14 (which was warmed to no more than 10° C. above its melting point).

EXAMPLE 33 (capsule)

| Component | % By Weight |
| --- | --- |
| Compound III (free base) | 15.01 |
| Propylene Glycol (NF) | 40.06 |
| p-toluenesulfonic acid, monohydrate, Sigma | 3.97 |
| Tween ® 80 | 5.05 |
| Ethanol (USP, 200 proof) | 2.52 |
| Polyethylene glycol 540 | 33.4 |

This composition was prepared according to the process of Example 31.

EXAMPLE 34 (capsule)

| Component | % By Weight |
| --- | --- |
| Compound III (free base) | 21.92 |
| Propylene Glycol (NF) | 25.64 |
| Hydrochloric acid, reagent | 5.85 |
| Cremophor ® RH40 | 3.76 |
| Miglyol ® 812 | 3.98 |
| Ethanol (USP, 200 proof) | 5.48 |
| Gelucire ® 44/14 | 33.4 |

This composition was prepared according to the process of Example 31 with the exception that the polyethylene glycol was replaced by Gelucire® 44/14 (which was warmed to no more than 10° C. above its melting point).

EXAMPLE 35 (capsule)

| Component | % By Weight |
| --- | --- |
| Compound III (free base) | 22.1 |
| Propylene glycol (NF) | 25.75 |
| Hydrochloric acid, reagent | 5.90 |
| Tween ® 80 | 3.66 |
| Miglyol ® 812 | 3.73 |
| Ethanol (USP, 200 proof) | 5.56 |
| Gelucire ® 44/14 | 33.3 |

This composition was prepared according to the process of Example 31 with the exception that the polyethylene glycol was replaced by Gelucire® 44/14 (which was warmed to no more than 10° C. above its melting point).

EXAMPLE 36 (capsule)

| Component | % By Weight |
| --- | --- |
| Compound III (free base) | 21.78 |
| Propylene Glycol (NF) | 19.91 |
| Hydrochioric acid, reagent | 5.96 |
| Cremophor ® RH40 | 6.82 |
| Miglyol ® 812 | 6.73 |
| Ethanol (USP, 200 proof) | 5.51 |
| Gelucire ® 44/14 | 33.28 |

Ethanol (27.7 g) and compound III (110 g, screened through a 16 mesh screen) were mixed in a stainless steel container until the solution was clear to slightly cloudy. Propylene glycol (100.4 g) was added and mixing continued until the solution was clear to slightly cloudy. Miglyol® (33.8 g) was added and mixed well. Cremophor® (34.3 g) was added and mixed well. The hydrochloric acid was then added and mixed well. This solution was placed in a water jacketed vessel (Vessel A) at a temperature of about 10° C.

The Gelucire® (168.1 g) was placed in a water jacketed vessel (Vessel B) and heated to melt the Gelucire®. The water jacket was then maintained at a temperature of about 75° C.

An H&K 330 capsule filling machine with a liquid fill attachment was then used to fill the composition into hard gelatin capsules (No. 00, iron gray opaque).

Each vessel was connected via a separate circulation line through a separate metering pump into a nozzle head/block through which the appropriate volume of the contents of each of Vessels A and B was pumped, mixed and filled into the capsules. The rate of flow through each of the metering pumps was adjusted to provide the appropriate ratio of the contents of each of Vessels A and B to obtain the desired final composition in the filled capsules. If necessary, the circulation lines and nozzle head/block were equipped with a heating/cooling jacket or line to allow for temperature adjustment during capsule filling.

EXAMPLE 37 (capsule)

| Component | % By Weight |
| --- | --- |
| Compound III (free base) | 18.03 |
| Propylene Glycol (NF) | 12.36 |
| Hydrochloric acid, reagent | 1.83 |
| Citric acid (USP, anhydrous, powder) | 4.12 |
| Tween ® 80 | 5.10 |
| Cremophor ® EL | 17.51 |
| Miglyol ® 812 | 2.58 |
| Ethanol (USP, 200 proof) | 5.13 |
| Gelucire ® 44/14 | 33.38 |

This composition was prepared according to the process of Example 31 with the exception that the polyethylene glycol was replaced by Gelucire® 44/14 (which was warmed to no more than 10° C. above its melting point).

EXAMPLE 38 (capsule)

| Component | % By Weight |
| --- | --- |
| Compound III (free base) | 17.84 |
| Propylene Glycol (NF) | 12.36 |
| Hydrochloric acid, reagent | 1.87 |
| Citric acid (USP, anhydrous, powder) | 4.08 |
| Tween ® 80 | 5.20 |
| Cremophor ® EL | 17.49 |
| Miglyol ® 812 | 2.69 |
| Ethanol (USP, 200 proof) | 5.13 |
| Gelucire ® 35/10 | 33.32 |

This composition was prepared according to the process of Example 31 with the exception that the polyethylene glycol was replaced by Gelucire® 35/10 (which was warmed to no more than 10° C. above its melting point).

EXAMPLE 39 (capsule)

| Component | By Weight |
| --- | --- |
| Compound III (free base) | 21.68 |
| Propylene Glycol (NF) | 19.77 |
| Hydrochloric acid, reagent | 6.06 |
| Cremophor ® EL | 6.87 |
| Miglyol ® 812 | 6.78 |
| Ethanol (USP, 200 proof) | 5.48 |
| Gelucire ® 35/10 | 33.36 |

This composition was prepared according to the process of Example 31 with the exception that the polyethylene glycol was replaced by Gelucire® 35/10 (which was warmed to no more than 10° C. above its melting point).

EXAMPLE 40 (capsule)

| Component | % By Weight |
| --- | --- |
| Compound III (free base) | 17.87 |
| Propylene Glycol (NF) | 12.12 |
| Hydrochloric acid, reagent | 1.92 |
| Citric acid (USP, anhydrous, powder) | 4.09 |
| Cremophor ® EL | 17.61 |
| Miglyol ® 812 | 2.56 |
| Tween ® 80 | 5.38 |
| Ethanol (USP, 200 proof) | 5.18 |
| Gelucire ® 46/07 | 33.28 |

This composition was prepared according to the process of Example 31 with the exception that the polyethylene glycol was replaced by Gelucire® 46/07 (which was warmed to no more than 10° C. above its melting point).

EXAMPLE 41 (capsule)

| Component | % By Weight |
| --- | --- |
| Compound III (free base) | 18.05 |
| Propylene Glycol (NF) | 12.42 |
| Hydrochloric acid, reagent | 1.87 |
| Citric acid (USP, anhydrous, powder) | 4.11 |
| Cremophor ® EL | 17.40 |
| Miglyol ® 812 | 2.61 |
| Tween ® 80 | 5.00 |
| Ethanol (USP, 200 proof) | 5.08 |
| Gelucire ® 50/13 | 33.46 |

This composition was prepared according to the process of Example 31 with the exception that the polyethylene glycol was replaced by Gelucire® 50/13 (which was warmed to no more than 10° C. above its melting point).

EXAMPLE 42 (capsule)

| Component | % By Weight |
| --- | --- |
| Compound III (free base) | 18.00 |
| Propylene Glycol (NF) | 12.31 |
| Hydrochloric acid, reagent | 1.90 |
| Citric acid (USP, anhydrous, powder) | 4.12 |
| Cremophor ® EL | 17.65 |
| Miglyol ® 812 | 2.56 |
| Tween ® 80 | 5.10 |
| Ethanol (USP, 200 proof) | 5.17 |
| Gelucire ® 50/13 | 25.04 |
| Neobee Oil M-5 | 8.35 |

This composition was prepared according to the process of Example 31 with the exception that the polyethylene glycol was replaced by Gelucire® 50/13 (which was warmed to no more than 10° C. above its melting point) and that the Neobee Oil was added to the melted Gelucire® 50/13. This mixture was added to the solution resulting from Step 1.

EXAMPLE 43 (capsule)

| Component | % By Weight |
| --- | --- |
| Compound III (free base) | 17.83 |
| Propylene Glycol (NF) | 12.20 |
| Hydrochloric acid, reagent | 1.88 |
| Citric acid (USP, anhydrous, powder) | 4.08 |
| Cremophor ® EL | 17.48 |
| Miglyol ® 812 | 2.54 |
| Tween ® 80 | 5.02 |
| Ethanol (USP, 200 proof) | 5.12 |
| Gelucire ® 50/13 | 17.22 |
| Gelucire ® 35/10 | 16.64 |

This composition was prepared according to the process of Example 31 with the exception that the polyethylene glycol was replaced by a mixture of Gelucire® 50/13 and Gelucire® 35/10 (which was warmed to no more than 10° C. above its melting point).

EXAMPLE 44 (capsule)

| Component | % By Weight |
| --- | --- |
| Compound III (free base) | 19.88 |
| Citric acid (USP, anhydrous, powder) | 2.01 |
| Ethanol (USP, 200 prool) | 8.12 |
| Gelucire ® 50/13 | 25.02 |
| Neobee Oil M-5 | 24.86 |
| N-methylpyrrolidinone | 12.07 |
| Vitamin E PEG 1000 succinate | 8.04 |

Step 1. The compound of formula III was mixed with the N-methylpyrrolidone. To this mixture was added with mixing the ethanol and all of the remaining ingredients (except the Gelucire® 50/13 and the Neobee Oil).

Step 2. The Gelucire® 50/13 was warmed (to no more than 10° C. above its melting point) until it was liquified. The liquified Gelucire® 50/13 was mixed with the Neobee Oil and this mixture was then added with mixing to the solution resulting from Step 1. The appropriate volume of this final mixture to provide the desired dose of compound III was filled into hard gelatin capsules.

EXAMPLE 45 (capsule)

| Component | % By Weight |
| --- | --- |
| Compound III (free base) | 19.57 |
| Citric acid (USP, anhydrous, powder) | 1.99 |
| Tween ® 80 | 5.94 |
| Ethanol (USP, 200 proof) | 7.85 |
| Gelucire ® 44/14 | 32.28 |
| N-methylpyrrolidinone | 11.71 |
| Vitamin E PEG 1000 succinate | 4.92 |
| Propyleneglycol monolaurate | 14.73 |
| Microcrystalline wax | 1.00 |

Step 1. The compound of formula III was mixed with the N-methylpyrrolidinone. To this mixture was added with mixing the ethanol and all of the remaining ingredients (except the Gelucire® 44/14).

Step 2. The Gelucire® 44/14 was warmed (to no more than 10° C. above its melting point) until it was liquified. The liquified Gelucire® 44/14 was then added with mixing to the solution resulting from Step 1. The appropriate volume of this final mixture to provide the desired dose of compound III was filled into hard gelatin capsules.

EXAMPLE 46 (capsule)

| Component | % By Weight |
| --- | --- |
| Compound III (free base) | 18.20 |
| Propylene Glycol (NF) | 12.47 |
| Hydrochloric acid, reagent | 1.26 |
| Cremophor ® EL | 11.23 |
| Miglyol ® 812 | 5.03 |
| Tween ® 80 | 5.13 |
| Ethanol (USP, 200 proof) | 14.11 |
| Gelucire ® 44/14 | 32.54 |

This composition was prepared according to the process of Example 31 with the exception that the polyethylene glycol was replaced by Gelucire® 44/14 (which was warmed to no more than 10° C. above its melting point).

EXAMPLE 47 (capsule)

| Component | % By Weight |
| --- | --- |
| Compound III (free base) | 18.22 |
| Propylene Glycol (NF) | 12.49 |
| Hydrochloric acid, reagent | 1.26 |
| Cremophor ® EL | 11.24 |
| Miglyol ® 812 | 5.05 |
| Tween ® 80 | 5.14 |
| Ethanol (USP, 200 proof) | 14.12 |
| Gelucire ® 50/13 | 32.46 |

This composition was prepared according to the process of Example 31 with the exception that the polyethylene glycol was replaced by Gelucire® 50/13 (which was warmed to no more than 10° C. above its melting point).

EXAMPLE 48 (capsule)

| Component | % By Weight |
| --- | --- |
| Compound III (free base) | 17.72 |
| Propylene Glycol (NF) | 14.73 |
| Hydrochloric acid, reagent | 2.33 |
| Cremophor ® EL | 11.81 |
| Miglyol ® 812 | 7.86 |
| Ethanol (USP, 200 proof) | 12.07 |
| Gelucire ® 44/14 | 33.48 |

This composition was prepared according to the process of Example 31 with the exception that the polyethylene glycol was replaced by Gelucire® 44/14 (which was warmed to no more than 10° C. above its melting point).

EXAMPLE 49 (capsule)

| Component | % By Weight |
| --- | --- |
| Compound III (free base) | 17.65 |
| Propylene Glycol (NF) | 14.67 |
| Hydrochloric acid, reagent | 2.32 |
| Cremophor ® EL | 11.76 |
| Miglyol ® 812 | 7.83 |
| Ethanol (USP, 200 proof) | 12.02 |
| Gelucire ® 50/13 | 33.73 |

This composition was prepared according to the process of Example 31 with the exception that the polyethylene glycol was replaced by Gelucire® 50/13 (which was warmed to no more than 10° C. above its melting point).

EXAMPLE 50 (capsule)

| Component | % By Weight |
| --- | --- |
| Compound III (free base) | 19.62 |
| Citric acid (USP, anhydrous, powder) | 2.00 |
| N-methylpyrrolidinone | 10.94 |
| Tween ® 80 | 5.05 |
| Vitamin E PEG 1000 succinate | 4.95 |
| propyleneglycol monolaurate | 14.62 |
| Ethanol (USP, 200 proof) | 8.03 |
| Gelucire ® 44/14 | 33.76 |
| Cab-o-sil ® | 1.03 |

The N-methylpyrrolidinone, Tween® 80, vitamin E PEG 1000 succinate and propyleneglycol monolaurate were mixed. The ethanol was added to the above mixture and stirred until the solution was clear to slightly cloudy. Then the citric acid was added and the mixture was stirred until it was clear to slightly cloudy. Compound III was added and the mixture was stirred until it was clear to slightly cloudy. The Gelucire® 44/14 was heated just enough to be liquified. The liquified Gelucire® 44/14 was added to the solution of the HIV protease inhibiting compound and stirred well. This solution was added slowly with mixing to the Cab-o-sil® and mixed well until the mixture was a dry solid. The resulting solid was passed through an appropriately sized seive to obtain granules. The appropriate amount of the granulation to provide the desired dose was filled into hard gelatin capsules.

EXAMPLE 51 (capsule)

| Component | % By Weight |
| --- | --- |
| Compound III (free base) | 16.99 |
| Propylene Glycol (NF) | 13.50 |
| Hydrochloric acid, reagent | 1.91 |
| Cremophor ® EL | 10.32 |
| Miglyol ® 812 | 4.99 |
| Tween ® 80 | 4.98 |
| Ethanol (USP, 200 proof) | 13.99 |
| Gelucire ® 50/13 | 33.30 |

This composition was prepared according to the process of Example 31 with the exception that the polyethylene glycol was replaced by Gelucire® 50/13 (which was warmed to no more than 10° C. above its melting point).

EXAMPLE 52 (capsule)

| Component | % By Weight |
| --- | --- |
| Compound III (free base) | 17.07 |
| Propylene Glycol (NF) | 14.00 |
| Hydrochloric acid, reagent | 1.90 |
| Cremophor ® EL | 10.05 |
| Miglyol ® 812 | 4.83 |
| Tween ® 80 | 4.79 |
| Ethanol (USP, 200 proof) | 13.95 |
| Gelucire ® 50/13 | 33.38 |

This composition was prepared according to the process of Example 31 with the exception that the polyethylene glycol was replaced by Gelucire® 50/13 (which was warmed to no more than 10° C. above its melting point).

EXAMPLE 53 (capsule)

| Component | % By Weight |
| --- | --- |
| Compound III (free base) | 17.96 |
| Propylene Glycol (NF) | 14.96 |
| Hydrochloric acid, reagent | 1.99 |
| Cremophor ® EL | 10.91 |
| Tween ® 80 | 5.90 |
| Ethanol (USP, 200 proof) | 14.98 |
| Gelucire ® 50/13 | 33.29 |

This composition was prepared according to the process of Example 31 with the exception that the polyethylene glycol was replaced by Gelucire® 50/13 (which was warmed to no more than 10° C. above its melting point).

EXAMPLE 54 (capsule)

| Component | % By Weight |
| --- | --- |
| Compound III (free base) | 13.00 |
| Propylene Glycol (NF) | 15.03 |
| Hydrochloric acid, reagent | 0.56 |
| Cremophor ® EL | 13.05 |
| Miglyol ® 812 | 5.18 |
| Tween ® 80 | 5.00 |
| Ethanol (USP, 200 proof) | 14.89 |
| Gelucire ® 50/13 | 33.30 |

This composition was prepared according to the process of Example 31 with the exception that the polyethylene glycol was replaced by Gelucire® 50/13 (which was warmed to no more than 10° C. above its melting point).

EXAMPLE 55 (capsule)

| Component | % By Weight |
| --- | --- |
| Compound III (free base) | 12.74 |
| Propylene Glycol (NF) | 10.73 |
| Hydrochloric acid, reagent | 0.94 |
| Cremophor ® EL | 17.78 |
| Miglyol ® 812 | 3.50 |
| Tween ® 80 | 5.31 |
| Ethanol (USP, 200 proof) | 5.03 |
| Gelucire ® 44/14 | 40.01 |

This composition was prepared according to the process of Example 31 with the exception that the polyethylene glycol was replaced by Gelucire® 44/14 (which was warmed to no more than 10° C. above its melting point).

EXAMPLE 56 (capsule)

| Component | % By Weight |
| --- | --- |
| Compound III (free base) | 12.45 |
| Propylene Glycol (NF) | 13.89 |
| Citric acid (USP, anhydrous, powder) | 4.19 |
| Cremophor ® EL | 16.00 |
| Miglyol ® 812 | 3.99 |
| Tween ® 80 | 5.99 |
| Ethanol (USP, 200 proof) | 10.06 |
| Gelucire ® 50/13 | 33.45 |

This composition was prepared according to the process of Example 31 with the exception that the polyethylene glycol was replaced by Gelucire® 50/13 (which was warmed to no more than 10° C. above its melting point).

EXAMPLE 57 (capsule)

| Component | % By Weight |
| --- | --- |
| Compound III (free base) | 20.0 |
| Propylene Glycol (NF) | 5.0 |
| Citric acid (USP, anhydrous, powder) | 4.0 |
| Cremophor ® EL | 12.0 |
| Miglyol ® 812 | 3.5 |
| Benzyl alcohol, NF | 5.0 |
| Tween ® 80 | 3.5 |
| Ethanol (USP, 200 proof) | 14.0 |
| Gelucire ® 50/13 | 33.0 |

Ethanol (105.0 g) was charged into a stainless steel container and mixing was begun. Citric acid (30.0 g) was added with mixing until a clear solution was obtained. Compound III (150 g) was added with mixing. Benzyl alcohol (37.5 g) and propylene glycol (37.5 g) were added with mixing and mixing continued until a clear solution was obtained. Cremophor® (90.0 g), Miglyol® (26.3 g) and Tween® 80 (26.3 g) were added and mixed well. This solution was placed in a water jacketed vessel (Vessel A) at a temperature of about 10° C.

The Gelucire® (247.5 g) was placed in a water jacketed vessel (Vessel B) and heated to melt the Gelucire®. The water jacket was then maintained at a temperature of about 10° C. above the melting point of the Gelucire®.

An H&K 330 capsule filling machine with a liquid fill attachment was then used to fill the composition into hard gelatin capsules (No. 00, iron gray opaque).

Each vessel was connected via a separate circulation line through a separate metering pump into a nozzle head/block through which the appropriate volume of the contents of each of Vessels A and B was pumped, mixed and filled into the capsules. The rate of flow through each of the metering pumps was adjusted to provide the appropriate ratio of the contents of each of Vessels A and B to obtain the desired final composition in the filled capsules. If necessary, the circulation lines and nozzle head/block were equipped with a heating/cooling jacket or line to allow for temperature adjustment during capsule filling.

EXAMPLE 58 (capsule)

| Component | % By Weight |
| --- | --- |
| Compound III (free base) | 12.86 |
| Propylene Glycol (NF) | 13.96 |
| Benzyl alcohol, NF | 4.01 |
| Cremophor ® EL | 16.81 |
| Miglyol ® 812 | 6.09 |
| Tween ® 80 | 6.94 |
| Ethanol (USP, 200 proof) | 6.01 |
| Gelucire ® 50/13 | 33.34 |

This composition was prepared according to the process of Example 31 with the exception that the polyethylene glycol was replaced by Gelucire® 50/13 (which was warmed to no more than 10° C. above its melting point).

EXAMPLE 59 (capsule)

| Component | % By Weight |
| --- | --- |
| Compound III (free base) | 17.70 |
| Propylene Glycol (NF) | 10.12 |
| Hydrochloric add, reagent | 2.67 |
| Cremophor ® EL | 18.29 |
| Migyol ® 812 | 5.94 |
| Tween ® 80 | 7.01 |
| Ethanol (USP, 200 proof) | 4.97 |
| Gelucire ® 50/13 | 33.31 |

This composition was prepared according to the process of Example 31 with the exception that the polyethylene glycol was replaced by Gelucire® 50/13 (which was warmed to no more than 10° C. above its melting point).

EXAMPLE 60 (capsule)

| Component | % By Weight |
| --- | --- |
| Compound III (free base) | 24.91 |
| Propylene Glycol (NF) | 10.08 |
| Hydrochloric acid, reagent | 3.92 |
| Cremophor ® EL | 7.95 |
| Miglyol ® 812 | 5.07 |
| Tween ® 80 | 4.87 |
| Benzyl alcohol, NF | 5.90 |
| Ethanol (USP, 200 proof) | 4.03 |
| Gelucire ® 50/13 | 33.28 |

This composition was prepared according to the process of Example 31 with the exception that the polyethylene glycol was replaced by Gelucire® 50/13 (which was warmed to no more than 10° C. above its melting point).

EXAMPLE 61 (capsule)

| Component | % By Weight |
| --- | --- |
| Compound III (free base) | 18.17 |
| Propylene Glycol (NF) | 6.16 |
| Hydrochloric acid, reagent | 1.82 |
| Cremophor ® EL | 17.02 |
| Miglyol ® 812 | 7.12 |
| Tween ® 80 | 6.98 |
| Benzyl alcohol, NF | 5.10 |
| Ethanol (USP, 200 proof) | 4.23 |
| Gelucire ® 50/13 | 33.40 |

This composition was prepared according to the process of Example 31 with the exception that the polyethylene glycol was replaced by Gelucire® 50/13 (which was warmed to no more than 10° C. above its melting point).

EXAMPLE 62 (capsule)

| Component | % By Weight |
| --- | --- |
| Compound III (free base) | 13.01 |
| Cremophor ® EL | 15.15 |
| Miglyol ® 812 | 5.15 |
| Tween ® 80 | 6.25 |
| 2-(2-ethoxyethoxy)ethanol | 17.03 |
| Ethanol (USP, 200 proof) | 10.04 |
| Gelucire ® 50/13 | 33.28 |

This composition was prepared according to the process of Example 31 with the exception that the polyethylene glycol was replaced by Gelucire® 50/13 (which was warmed to no more than 10° C. above its melting point).

EXAMPLE 63 (capsule)

| Component | % By Weight |
| --- | --- |
| Compound III (free base) | 18.20 |
| Propylene Glycol (NF) | 12.47 |
| Hydrochloric acid, reagent | 1.26 |
| Cremophor ® EL | 11.23 |
| Miglyol ® 812 | 5.03 |
| Tween ® 80 | 5.13 |
| Ethanol (USP, 200 proof) | 14.11 |
| Gelucire ® 44/14 | 32.54 |

This composition was prepared according to the process of Example 31 with the exception that the polyethylene glycol was replaced by Gelucire® 44/14 (which was warmed to no more than 10° C. above its melting point).

EXAMPLE 64 (capsule)

| Component | % By Weight |
| --- | --- |
| Compound III (free base) | 16.00 |
| Citric acid (USP, anhydrous, powder) | 2.01 |
| Cremophor ® EL | 5.05 |
| Dimethyl isosorbide | 31.93 |
| Miglyol ® 812 | 1.98 |
| Ethanol (USP, 200 proof) | 12.99 |
| Gelucire ® 44/14 | 30.04 |

This composition was prepared according to the process of Example 31 with the exception that the polyethylene glycol was replaced by Gelucire® 44/14 (which was warmed to no more than 10° C. above its melting point).

EXAMPLE 65 (capsule)

| Component | % By Weight |
| --- | --- |
| Compound III (free base) | 13.99 |
| Propylene Glycol (NF) | 3.54 |
| Citric acid (USP, anhydrous, powder) | 2.10 |
| Cremophor ® EL | 20.36 |
| Miglyol ® 812 | 2.08 |
| Tween ® 80 | 3.48 |
| Dimethyl isosorbide | 17.48 |
| Ethanol (USP, 200 proof) | 7.0 |
| Gelucire ® 50/13 | 29.97 |

This composition was prepared according to the process of Example 31 with the exception that the polyethylene glycol was replaced by Gelucire® 50/13 (which was warmed to no more than 10° C. above its melting point).

EXAMPLE 66 (capsule)

| Component | % By Weight |
| --- | --- |
| Compound III (free base) | 13.00 |
| Propylene Glycol (NF) | 7.02 |
| Citric acid (USP, anhydrous, powder) | 4.00 |
| Cremophor ® EL | 16.37 |
| Miglyol ® 812 | 4.68 |
| Tween ® 80 | 4.68 |

-continued

| Component | % By Weight |
| --- | --- |
| Ethanol (USP, 200 proof) | 17.77 |
| Gelucire ® 50/13 | 32.49 |

This composition was prepared according to the process of Example 31 with the exception that the polyethylene glycol was replaced by Gelucire® 50/13 (which was warmed to no more than 10° C. above its melting point).

EXAMPLE 67 (capsule)

| Component | % By Weight |
| --- | --- |
| Compound III (free base) | 14.12 |
| Propylene Glycol (NF) | 7.10 |
| Hydrochloric acid, reagent | 2.04 |
| Citric acid (USP, anhydrous, powder) | 3.03 |
| Cremophor ® EL | 20.12 |
| Miglyol ® 812 | 6.11 |
| Tween ® 80 | 6.10 |
| Ethanol (USP, 200 proof) | 8.05 |
| Gelucire ® 50/13 | 33.35 |

This composition was prepared according to the process of Example 31 with the exception that the polyethylene glycol was replaced by Gelucire® 50/13 (which was warmed to no more than 10° C. above its melting point).

EXAMPLE 68 (capsule)

| Component | % By Weight |
| --- | --- |
| Compound III (free base) | 19.89 |
| Propylene Glycol (NF) | 4.97 |
| Citric acid (USP, anhydrous, powder) | 2.99 |
| Cremophor ® EL | 19.86 |
| Miglyol ® 812 | 2.99 |
| Benzyl alcohol, NF | 4.98 |
| Tween ® 80 | 5.13 |
| Ethanol (USP, 200 proof) | 10.94 |
| Gelucire ® 50/13 | 33.37 |

This composition was prepared according to the process of Example 31 with the exception that the polyethylene glycol was replaced by Gelucire® 50/13 (which was warmed to no more than 10° C. above its melting point).

EXAMPLE 69 (capsule)

| Component | % By Weight |
| --- | --- |
| Compound III (free base) | 13.00 |
| Propylene Glycol (NF) | 6.50 |
| Citric acid (USP, anhydrous, powder) | 4.00 |
| Cremophor ® EL | 15.59 |
| Miglyol ® 512 | 4.68 |
| Tween ® 80 | 4.68 |
| Ethanol (USP, 200 proof) | 17.77 |
| Gelucire ® 50/13 | 33.79 |

Ethanol (136.75 g) and compound III (50 g, screened through a 16 mesh screen) were mixed in a stainless steel container until the solution was clear to slightly cloudy. Citric acid (15 g) was added with mixing. Compound III (50 g) was added with mixing. Citric acid (15.75 g) was added with mixing and mixing was continued until the solution was clear. Propylene glycol (50 g) was added with mixing and mixing continued until a uniform mixture was obtained. Cremophor® (120 g), Miglyol® (36 g) and Tween® 80 (36 g) were added and mixed well. This solution was placed in a water jacketed vessel (Vessel A) at a temperature of about 10° C.

The Gelucire® (260.0 g) was placed in a water jacketed vessel (Vessel B) and heated to melt the Gelucire®. The water jacket was then maintained at a temperature of about 10° C. above the melting point of the Gelucire®.

An H&K 330 capsule filling machine with a liquid fill attachment was then used to fill the composition into hard gelatin capsules (No. 00, iron gray opaque, PEG treated).

Each vessel was connected via a separate circulation line through a separate metering pump into a nozzle head/block through which the appropriate volume of the contents of each of Vessels A and B was pumped, mixed and filled into the capsules. The rate of flow through each of the metering pumps was adjusted to provide the appropriate ratio of the contents of each of Vessels A and B to obtain the desired final composition in the filled capsules. If necessary, the circulation lines and nozzle head/block were equipped with a heating/cooling jacket or line to allow for temperature adjustment during capsule filling.

EXAMPLE 70 (capsule)

| Component | % By Weight |
| --- | --- |
| Compound III (free base) | 12.88 |
| Propylene Glycol (NF) | 5.95 |
| Citric acid (USP, anhydrous, powder) | 2.97 |
| Cremophor ® EL | 19.83 |
| Miglyol ® 812 | 4.97 |
| Benzyl alcohol, NF | 3.05 |
| Tween ® 80 | 5.98 |
| Ethanol (USP, 200 proof) | 10.88 |
| Gelucire ® 50/13 | 33.49 |

This composition was prepared according to the process of Example 31 with the exception that the polyethylene glycol was replaced by Gelucire® 50/13 (which was warmed to no more than 10° C. above its melting point).

EXAMPLE 71 (capsule)

| Component | % By Weight |
| --- | --- |
| Compound III (free base) | 12.87 |
| Propylene Glycol (NF) | 5.98 |
| Citric acid (USP, anhydrous, powder) | 2.97 |
| Cremophor ® EL | 18.69 |
| Miglyol ® 812 | 4.02 |
| Benzyl alcohol, NF | 3.02 |
| Tween ® 80 | 5.02 |
| Ethanol (USP, 200 proof) | 13.93 |
| Gelucire ® 50/13 | 33.50 |

This composition was prepared according to the process of Example 31 with the exception that the polyethylene glycol was replaced by Gelucire® 50/13 (which was warmed to no more than 10° C. above its melting point).

EXAMPLE 72 (capsule)

| Component | % By Weight |
|---|---|
| Compound III (free base) | 18.9 |
| Propylene Glycol (NF) | 6.2 |
| Citric acid (USP, anhydrous, powder) | 3.0 |
| Cremophor ® EL | 9.4 |
| Benzyl alcohol, NF | 5.1 |
| Tween ® 80 | 4.7 |
| Ethanol (USP, 200 proof) | 14.2 |
| Sulfuric acid, reagent grade | 0.5 |
| Sorbitan monolaurate, NF | 4.6 |
| Sorbitan monooleate, NF | 4.9 |
| Dimethyl isosorbide | 4.4 |
| Gelucire ® 50/13 | 24.1 |

This composition was prepared according to the process of Example 31 with the exception that the polyethylene glycol was replaced by Gelucire® 50/13 (which was warmed to no more than 10° C. above its melting point).

EXAMPLE 73 (capsule)

| Component | % By Weight |
|---|---|
| Compound III (free base) | 12.90 |
| Propylene Glycol (NF) | 5.99 |
| Citric acid (USP, anhydrous, powder) | 3.01 |
| Cremophor ® EL | 12.90 |
| Miglyol ® 812 | 4.98 |
| Benzyl alcohol, NF | 3.30 |
| Tween ® 80 | 6.03 |
| Ethanol (USP, 200 proof) | 13.89 |
| Gelucire ® 50/13 | 37.00 |

Ethanol (107.7 g) was charged into a stainless steel container and mixing was begun. Benzyl alcohol (23.1 g) and citric acid (23.1 g) were added with mixing. Compound III (100 g) was added with mixing. Propylene glycol (46.2 g) was added with mixing and mixing continued until a clear solution was obtained. Cremophor® (138.5 g), Miglyol® (38.5 g) and Tween® 80 (38.5 g) were added and mixed well. This solution was placed in a water jacketed vessel (Vessel A) at a temperature of about 10° C.

The Gelucire® (253.9 g) was placed in a water jacketed vessel (Vessel B) and heated to melt the Gelucire®. The water jacket was then maintained at a temperature of about 10° C. above the melting point of the Gelucire®.

An H&K 330 capsule filling machine with a liquid fill attachment was then used to fill the composition into hard gelatin capsules (No. 00, iron gray opaque).

Each vessel was connected via a separate circulation line through a separate metering pump into a nozzle head/block through which the appropriate volume of the contents of each of Vessels A and B was pumped, mixed and filled into the capsules. The rate of flow through each of the metering pumps was adjusted to provide the appropriate ratio of the contents of each of Vessels A and B to obtain the desired final composition in the filled capsules. If necessary, the circulation lines and nozzle head/block were equipped with a heating/cooling jacket or line to allow for temperature adjustment during capsule filling.

EXAMPLE 74 (capsule)

| Component | % By Weight |
|---|---|
| Compound III (free base) | 23.6 |
| Propylene Glycol (NF) | 9.90 |
| Citric acid (USP, anhydrous, powder) | 2.90 |
| Cremophor ® EL | 8.83 |
| Miglyol ® 812 | 2.03 |
| Benzyl alcohol, NF | 4.94 |
| Tween ® 80 | 4.7 |
| Ethanol (USP, 200 proof) | 9.77 |
| Sulfuric acid, reagent grade | 0.54 |
| Sorbitan monolaurate, NF | 2.92 |
| Sorbitan monooleate, NF | 1.86 |
| Dimethyl isosorbide | 2.43 |
| Gelucire ® 50/13 | 28.10 |

This composition was prepared according to the process of Example 31 with the exception that the polyethylene glycol was replaced by Gelucire® 50/13 (which was warmed to no more than 10° C. above its melting point).

EXAMPLE 75 (capsule)

| Component | % By Weight |
|---|---|
| Compound III (free base) | 24.27 |
| Propylene Glycol (NF) | 5.86 |
| Citric acid (USP, anhydrous, powder) | 3.14 |
| Cremophor ® EL | 6.80 |
| Miglyol ® 812 | 4.00 |
| Benzyl alcohol, NF | 4.82 |
| Ethanol (USP, 200 proof) | 13.58 |
| Sulfuric acid, reagent grade | 0.53 |
| Sorbitan monolaurate, NF | 2.40 |
| Sorbitan monooleate, NF | 2.00 |
| Dimethyl isosorbide | 2.49 |
| Gelucire ® 50/13 | 30.11 |

This composition was prepared according to the process of Example 31 with the exception that the polyethylene glycol was replaced by Gelucire® 50/13 (which was warmed to no more than 10° C. above its melting point).

EXAMPLE 76 (capsule)

| Component | % By Weight |
|---|---|
| Compound III (free base) | 19.92 |
| Propylene Glycol (NF) | 6.01 |
| Citric acid (USP, anhydrous, powder) | 3.00 |
| Cremophor ® EL | 9.00 |
| Benzyl alcohol, NF | 5.00 |
| Tween ® 80 | 4.7 |
| Ethanol (USP, 200 proof) | 13.90 |
| Sulfuric acid, reagent grade | 0.53 |
| Sorbitan monolaurate, NF | 2.04 |
| Sorbitan monooleate, NF | 2.10 |
| Dimethyl isosorbide | 4.5 |
| Gelucire ® 50/13 | 32.00 |

This composition was prepared according to the process of Example 31 with the exception that the polyethylene glycol was replaced by Gelucire® 50/13 (which was warmed to no more than 10° C. above its melting point).

EXAMPLE 77 (capsule)

| Component | % By Weight |
|---|---|
| Compound III (free base) | 19.82 |
| Propylene Glycol (NF) | 4.93 |
| Citric acid (USP, anhydrous, powder) | 3.96 |
| Cremophor ® EL | 11.97 |
| Miglyol ® 812 | 3.54 |
| Benzyl alcohol, NF | 4.98 |
| Tween ® 80 | 3.46 |
| Ethanol (USP, 200 proof) | 13.85 |
| Gelucire ® 50/13 | 33.48 |

This composition was prepared according to the process of Example 31 with the exception that the polyethylene glycol was replaced by Gelucire® 50/13 (which was warmed to no more than 10° C. above its melting point).

EXAMPLE 78 (capsule)

| Component | % By Weight |
|---|---|
| Compound III (free base) | 25.0 |
| Propylene Glycol (NF) | 6.0 |
| Citric acid (USP, anhydrous, powder) | 3.0 |
| Cremophor ® EL | 9.0 |
| Miglyol ® 812 | 2.0 |
| Tween ® 80 | 2.0 |
| Ethanol (USP, 200 proof) | 14.0 |
| Benzyl alcohol, NF | 5.o |
| Sulfuric acid, reagent grade | 0.5 |
| Sorbitan monooleale, NF | 2.0 |
| Dimethyl isosorbide | 2.5 |
| Gelucire ® 50/13 | 29.0 |

Ethanol (112.0 g) was charged into a stainless steel container and mixing was begun. Citric acid (24.0 g) was added with mixing and mixed until a clear solution was obtained. Benzyl alcohol (40.0 g), dimethyl isosorbide (20.0 g) and propylene glycol (48.0 g) were added with mixing and mixing continued until a clear solution was obtained. Compound III (200 g) was added with mixing. Sulfuric acid (4.0 g) was added with mixing and mixed until a clear solution was obtained. Cremophor® (72.0 g), Miglyol® (16.0 g), sorbitan monooleate (16.0 g) and Tween® 80 (16.0 g) were added and mixed well. This solution was placed in a water jacketed vessel (Vessel A) at a temperature of about 22° C.

The Gelucire® (232.0 g) was placed in a water jacketed vessel (Vessel B) and heated to melt the Gelucire®. The water jacket was then maintained at a temperature of about 10° C. above the melting point of the Gelucire®.

An H&K 330 capsule filling machine with a liquid fill attachment was then used to fill the composition into hard gelatin capsules (No. 00, iron gray opaque).

Each vessel was connected via a separate circulation line through a separate metering pump into a nozzle head/block through which the appropriate volume of the contents of each of Vessels A and B was pumped, mixed and filled into the capsules. The rate of flow through each of the metering pumps was adjusted to provide the appropriate ratio of the contents of each of Vessels A and B to obtain the desired final composition in the filled capsules. If necessary, the circulation lines and nozzle head/block were equipped with a heating/cooling jacket or line to allow for temperature adjustment during capsule filling.

EXAMPLE 79 (capsule)

| Component | % By Weight |
|---|---|
| Compound III (free base) | 25.0 |
| Propylene Glycol (NF) | 4.0 |
| Citric acid (USP, anhydrous, powder) | 5.0 |
| Cremophor ® EL | 9.0 |
| Miglyol ® 812 | 2.0 |
| Tween ® 80 | 2.0 |
| Ethanol (USP, 200 proof) | 17.0 |
| Benzyl alcohol, NF | 7.0 |
| Gelucire ® 50/13 | 29.0 |

Ethanol (136.0 g) was charged into a stainless steel container and mixing was begun. Citric acid (40.0 g) was added with mixing and mixed until a clear solution was obtained. Compound III (200 g) was added with mixing. Benzyl alcohol (56.0 g) was added with mixing and mixing continued until a clear solution was obtained. Propylene glycol (32.0 g) were added with mixing and mixing continued until a clear solution was obtained. Cremophor® (72.0 g), Miglyol® (16.0 g) and Tween® 80 (16.0 g) were added and mixed well. This solution was placed in a water jacketed vessel (Vessel A) at a temperature of about 22° C.

The Gelucire® (232.0 g) was placed in a water jacketed vessel (Vessel B) and heated to melt the Gelucire®. The water jacket was then maintained at a temperature of about 10° C. above the melting point of the Gelucire®.

An H&K 330 capsule filling machine with a liquid fill attachment was then used to fill the composition into hard gelatin capsules (No.00, iron gray opaque).

Each vessel was connected via a separate circulation line through a separate metering pump into a nozzle head/block through which the appropriate volume of the contents of each of Vessels A and B was pumped, mixed and filled into the capsules. The rate of flow through each of the metering pumps was adjusted to provide the appropriate ratio of the contents of each of Vessels A and B to obtain the desired final composition in the filled capsules. If necessary, the circulation lines and nozzle head/block were equipped with a heating/cooling jacket or line to allow for temperature adjustment during capsule filling.

Compound III can be prepared according to the procedures disclosed in PCT Patent Application No. WO94/14436, published Jul. 7, 1994 and U.S. patent application Ser. No. 158,587, filed Dec. 2, 1993, both of which are incorporated herein by reference.

Protocol For Oral Bioavailability Studies

Dogs (beagle dogs, mixed sexes, weighing 7–14 kg) were fasted overnight prior to dosing, but were permitted water adlibitum. Each dog received a 100 µg/kg subcutaneous dose of histamine approximately 30 minutes prior to dosing. Each dog received a single solid dosage form corresponding to a 5 mg/kg dose of the drug. The dose was followed by approximately 10 milliliters of water. Blood samples were obtained from each animal prior to dosing and 0.25, 0.5, 1.0, 1.5, 2, 3, 4, 6, 8, 10 and 12 hours after drug administration. The plasma was separated from the red cells by centrifugation and frozen (−30° C.) until analysis. Concentrations of parent drug were determined by reverse phase HPLC with low wavelength UV detection following liquid-liquid extraction of the plasma samples. The parent drug area under the curve was calculated by the trapezoidal method over the time course of the study. The absolute bioavailability of each test composition was calculated by comparing the area under the curve after oral dosing to that obtained from a single intravenous dose. Each capsule or capsule composition was evaluated in a group containing at least six dogs; the values reported are averages for each group of dogs. The average bioavailability data for the compositions of the Examples is shown in Table I.

TABLE 1

| Example No. | Mean % Bioavailability |
| --- | --- |
| Example 1 | 0.0 |
| Example 2 | 0.0 |
| Example 3 | 2.5 |
| Example 4 | 37.4 |
| Example 5 | 36.2 |
| Example 6 | 55.7 |
| Example 7 | 42.1 |
| Example 8 | 87.8 |
| Example 9 | 58.4 |
| Example 10 | 25.8 |
| Example 11 | 64.1 |
| Example 12 | 100 |
| Example 13 | 39.6 |
| Example 14 | 93.9 |
| Example 15 | 73.4 |
| Example 16 | 76.8 |
| Example 17 | 94.1 |
| Example 18 | 73.3 |
| Example 20 | 56.0 |
| Example 21 | 100 |
| Example 22 | 53.3 |
| Example 23 | 52.4 |
| Example 24 | 58.5 |
| Example 25 | 69.9 |
| Example 26 | 54.0 |
| Example 27 | 100 |
| Example 28 | 93.3 |
| Example 29 | 55.5 |
| Example 31 | 53.3 |
| Example 32 | 52.4 |
| Example 33 | 58.5 |
| Example 34 | 69.9 |
| Example 35 | 54.0 |
| Example 36 | 100 |
| Example 37 | 93.3 |
| Example 38 | 89.6 |
| Example 39 | 100 |
| Example 40 | 61.5 |
| Example 41 | 76.2 |
| Example 42 | 82.4 |
| Example 43 | 75.7 |
| Example 44 | 49.9 |
| Example 45 | 84.1 |
| Example 46 | 79.2 |
| Example 47 | 100 |
| Example 51 | 100 |
| Example 52 | 93.2 |
| Example 53 | 61.5 |
| Example 54 | 76.4 |
| Example 55 | 54.9 |
| Example 56 | 96.7 |
| Example 58 | 77.8 |
| Example 59 | 100 |
| Example 60 | 51 |
| Example 61 | 91.4 |
| Example 62 | 46.8 |
| Example 63 | 79.2 |
| Example 64 | 87.4 |
| Example 65 | 100 |
| Example 66 | 100 |
| Example 67 | 100 |
| Example 68 | 87.4 |
| Example 69 | 99.3 |
| Example 70 | 100 |
| Example 71 | 63.2 |
| Example 72 | 98.6 |
| Example 73 | 96.0 |

TABLE 1-continued

| Example No. | Mean % Bioavailability |
| --- | --- |
| Example 74 | 67.7 |
| Example 75 | 41.7 |
| Example 76 | 81.9 |
| Example 77 | 87.3 |

This data indicates that solution compositions provided significantly better bioavailability than non-formulated compound III. Additionally, the solution composition, encapsulated in hard gelatin capsule or soft elastic capsule, demonstrated greatly improved bioavailability. Additionally, the solid composition, encapusaled in a gelatin capsule, demonstrated greatly improved bioavailability.

Compounds I, II and III are inhibitors of HIV-1 and HIV-2 protease. They are useful for inhibiting an HIV infection and treating AIDS in humans. Total daily dose of compound I, II or III administered to a human in single or divided doses may be in amounts, for example, from 0.001 to 1000 mg/kg body weight daily but more usually 0.1 to 50 mg/kg body weight daily. Dosage unit compositions may contain such amounts of submultiples thereof to make up the daily dose. It will be understood, however, that the specific dose level for any particular patient will depend upon a variety of factors including the age, body weight, general health, sex, diet, time of administration, rate of excretion, drugs administered in combination and the severity of the particular disease undergoing therapy.

The foregoing is merely illustrative of the invention and is not intended to limit the invention to the disclosed compounds, methods and compositions. Variations and changes which are obvious to one skilled in the art are intended to be within the scope and nature of the invention which are defined in the appended claims.

What is claimed is:

1. A pharmaceutical composition comprising a solution of a compound of the formula:

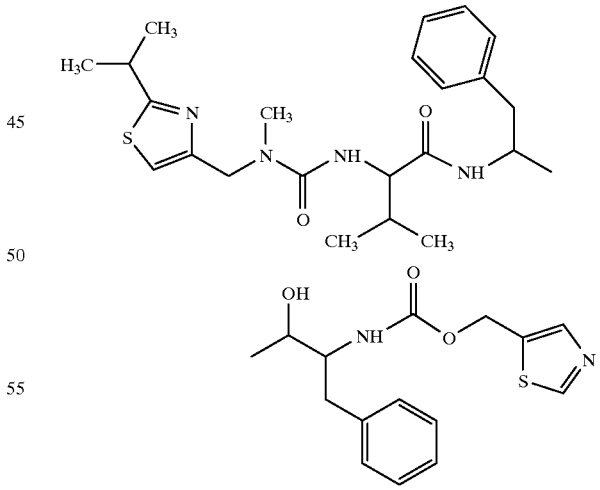

in (i) a pharmaceutically acceptable organic solvent which is a pharmaceutically acceptable alcohol or (ii) a mixture of pharmaceutically acceptable organic solvents wherein the mixture comprises a pharmaceutically acceptable alcohol.

2. The composition of claim 1 wherein the solution is encapsulated in a hard gelatin capsule or a soft elastic gelatin capsule.

3. The composition of claim 1 further comprising a pharmaceutically acceptable acid.

4. The composition of claim 1 further comprising an additive or a mixture of additives independently selected from the group consisting of glycerin, pharmaceutically acceptable surfactants and antioxidants.

5. A pharmaceutical composition comprising a solution of (a) a compound of the formula:

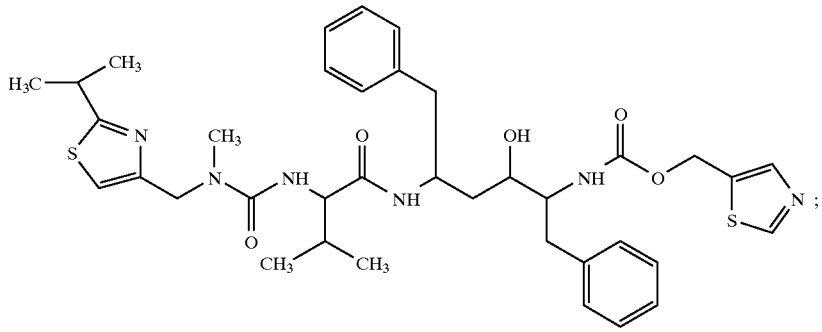

and (b) a pharmaceutically acceptable acid or a combination of pharmaceutically acceptable acids in (i) a pharmaceutically acceptable organic solvent which is a pharmaceutically acceptable alcohol or (ii) a mixture of pharmaceutically acceptable organic solvents wherein the mixture comprises a pharmaceutically acceptable alcohol.

6. The composition of claim 5 wherein the solution is encapsulated in a hard gelatin capsule or a soft elastic gelatin capsule.

7. The composition of claim 5 further comprising water.

8. The composition of claim 5 further comprising an additive or a mixture of additives independently selected from the group consisting of glycerin, pharmaceutically acceptable surfactants and antioxidants.

9. The composition of claim 5 comprising a solution of (a) about 8.8% by weight of the total solution of (2S,3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane; and (b) about 2 molar equivalents, based upon the amount of the compound of part (a), of hydrochloric acid in a mixture of propylene glycol in the amount of about 82% by weight of the total solution, ethanol in the amount of about 3.5% by weight of the total solution and water in the amount of about 4.4% by weight of the total solution.

10. The composition of claim 9 wherein the solution is encapsulated in a hard gelatin capsule.

11. The composition of claim 5 comprising a solution of (1) (2S,3S,5S)-5-(N-(N-((N-Methyl-N-((2-isopropyl-4-thiazolyl)methyl)-amino)carbonyl)-valinyl)amino)-2-(N-((5-thiazolyl)methoxycarbonyl)amino)-1,6-diphenyl-3-hydroxyhexane in the amount of from about 2% to about 30% by weight of the total solution and (2) a total of from about 0.2 to about 2 molar equivalents (based on the compound of part (1)) of (i) a pharmaceutically acceptable acid or (ii) a mixture of pharmaceutically acceptable acids in a mixture of (a) a pharmaceutically acceptable alcohol or mixture of pharmaceutically acceptable alcohols in a total amount of from about 2% to about 50% by weight of the total solution, said alcohol or mixture of alcohols being a liquid at room temperature and (b) a pharmaceutically acceptable organic solvent or a mixture of pharmaceutically acceptable organic solvents in a total amount of from about 20% to about 60% by weight of the total solution, said solvent or mixture of solvents having a melting point between about 20° C. and about 60° C., said solvent or mixture of solvents being miscible with the alcohol or mixture of alcohols and providing a homogeneous mixture with the alcohol or mixture of alcohols, said homogeneous mixture being a solid or semi-solid at about 20° C., wherein the solution is encapsulated in a soft elastic capsule or a hard gelatin capsule.

12. The composition of claim 11 comprising a solution of (1) (2S,3S,5S)-5-(N-(N-((N-Methyl-N-((2-isopropyl-4-thiazolyl)methyl)-amino)carbonyl)-valinyl)amino)-2-(N-((5-thiazolyl)methoxycarbonyl)amino)-1,6-diphenyl-3-hydroxyhexane in the amount of from about 2% to about 30% by weight of the total solution and (2) a total of from about 0.2 to about 2 molar equivalents (based on the compound of part (1)) of (i) a pharmaceutically acceptable acid or (ii) a mixture of pharmaceutically acceptable acids in a mixture of (a) propylene glycol in the amount of from about 4% to about 40% by weight of the total solution, (b) ethanol in the amount of from about 2% to about 20% by weight of the total solution, and (c) polyethylene glycol 540 in the amount of from about 20% to about 60% by weight of the total solution or a total amount of from about 20% to about 60% by weight of the total solution of (i) a saturated polyglycolized glyceride or (ii) a mixture of saturated polyglycolized glycerides, wherein the solution is encapsulated in a soft elastic capsule or a hard gelatin capsule.

13. The composition of claim 12 comprising a solution of (1) (2S,3S,5S)-5-(N-(N-((N-Methyl-N-((2-isopropyl-4-thiazolyl)methyl)-amino)carbonyl)-valinyl)amino)-2-(N-((5-thiazolyl)methoxycarbonyl)amino)-1,6-diphenyl-3-hydroxyhexane in the amount of from about 20% to about 25% by weight of the total solution and (2) a total of from about 1.5 to about 2 molar equivalents (based on the compound of part (1)) of hydrochloric acid in a mixture of (a) propylene glycol in the amount of from about 20% to about 22% by weight of the total solution, (b) ethanol in the amount of from about 5% to about 6% by weight of the total solution, and (c) a saturated polyglycolized glyceride in the amount of from about 30% to about 35% by weight of the total solution, wherein the solution is encapsulated in a hard gelatin capsule.

14. The composition of claim 12 comprising a solution of (1) (2S,3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3- hydroxyhexane in the amount of from about 15% to about 20% by weight of the total solution and (2) a total of from about 0.3 to about 0.6 molar equivalents (based on the compound of part (1)) of hydrochloric acid in a mixture of (a) propylene glycol in the amount of about 12% by weight of the total solution, (b) ethanol in the amount of from about 5% to about 6% by weight of the total solution, and (c) a saturated polyglycolized glyceride in the amount of from about 30% to about 35% by weight of the total solution, wherein the solution is encapsulated in a hard gelatin capsule.

15. The composition of claim 12 comprising a solution of: (1) (2S,3S,5S)-5-(N-(N-((N-Methyl-N-((2-isopropyl-4-thiazolyl)methyl)-amino)carbonyl)-valinyl)amino)-2-(N-((5-thiazolyl)-methoxycarbonyl)amino)-1,6-diphenyl-3-hydroxyhexane in the amount of from about 15% to about 20% by weight of the total solution in a mixture of (a) propylene glycol in the amount of about 40% by weight of the total solution, (b) ethanol in the amount of about 2% to about 3% by weight of the total solution, and (c) polyethylene glycol 540 in the amount of from about 30% to about 35% by weight of the total solution, wherein the solution is encapsulated in a hard gelatin capsule.

16. The composition of claim 12 comprising a solution of (1) (2S,3S,5S)-5-(N-(N-((N-Methyl-N-((2-isopropyl-4-thiazolyl)methyl)-amino)carbonyl)-valinyl)amino)-2-(N-((5-thiazolyl)methoxycarbonyl)amino)-1,6-diphenyl-3-hydroxyhexane in the amount of from about 15% to about 20% by weight of the total solution and (2) a total of from about 0.3 to about 0.6 molar equivalents (based on the compound of part (1)) of hydrochloric acid in a mixture of (a) propylene glycol in the amount of about 12% by weight of the total solution, (b) ethanol in the amount of from about 10% to about 15% by weight of the total solution, and (c) a saturated polyglycolized glyceride in the amount of from about 30% to about 35% by weight of the total solution, wherein the solution is encapsulated in a hard gelatin capsule.

17. The composition of claim 12 comprising a solution of (1) (2S,3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)amino)-1,6-diphenyl-3-hydroxyhexane in the amount of from about 4% to about 30% by weight of the total solution and (2) a total of about two molar equivalents (based on the compound (1)) of (i) a pharmaceutically acceptable acid or (ii) a mixture of pharmaceutically acceptable acids in a mixture of (a) propylene glycol in the amount of from about 10% to about 40% by weight of the total solution, (b) ethanol in the amount of from about 2% to about 8%, and (c) polyethylene glycol 540 in the amount of from about 25% to about 60% by weight of the total solution or saturated polyglycolized glyceride in the amount of from about 25% to about 60% by weight of the total solution.

18. The composition of claim 17 wherein the solution is encapsulated in a hard gelatin capsule.

19. The composition of claim 12 comprising a solution of (1) (2S,3S,5S)-5-(N-(N-((N-Methyl-N-((2-isopropyl-4-thiazolyl)methyl)-amino)carbonyl)-valinyl)amino)-2-(N-((5-thiazolyl)methoxycarbonyl)amino)-1,6-diphenyl-3-hydroxyhexane in the amount of from about 20% to about 25% by weight of the total solution and (2) a total of about two molar equivalents (based on the compound of part (1)) of hydrochloric acid in a mixture of (a) propylene glycol in the amount of from about 22% by weight of the total solution, (b) ethanol in the amount of from about 5% to about 6% by weight of the total solution, and (c) saturated polyglycolized glyceride in the amount of from about 30% to about 35% by weight of the total solution.

20. The composition of claim 19 wherein the solution is encapsulated in a hard gelatin capsule.

21. The composition of claim 12 comprising a solution of: (1) (2S,3S,5S)-5-(N-(N-((N-Methyl-N-((2-isopropyl-4-thiazolyl)methyl)-amino)carbonyl)-valinyl)amino)-2-(N-((5-thiazolyl)methoxycarbonyl)amino)-1,6-diphenyl-3-hydroxyhexane in the amount of from about 15% to about 20% by weight of the total solution and (2) a total of about two molar equivalents (based on the compound (1)) of a mixture of citric acid and hydrochloric acid in a mixture of (a) propylene glycol in the amount of about 12% by weight of the total solution, (b) ethanol in the amount of from about 5% to about 6% by weight of the total solution, and (c) a saturated polyglycolized glyceride in the amount of from about 30% to about 35% by weight of the total solution.

22. The composition of claim 21 wherein the solution is encapsulated in a hard gelatin capsule.

23. The composition of claim 12 comprising a solution of (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of from about 15% to about 20% by weight of the total solution and (2) a total of about two molar equivalents (based on the compound (1)) of p-toluene-sulfonic acid in a mixture of (a) propylene glycol in the amount of about 40% by weight of the total solution, (b) ethanol in the amount of from about 2% to about 3% by weight of the total solution, and (c) polyethylene glycol 540 in the amount of from about 30% to about 35% by weight of the total solution.

24. The composition of claim 23 wherein the solution is encapsulated in a hard gelatin capsule.

25. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of about 22% by weight of the total solution and (2) a total of about 1.6 molar equivalents (based on the compound (1)) of hydrochloric acid in a mixture of (a) propylene glycol in the amount of about 20% by weight of the total solution, (b) ethanol in the amount of from about 5% to about 6% by weight of the total solution, and (c) a saturated polyglycolized glyceride in the amount of from about 30% to about 35% by weight of the total solution.

26. The composition of claim 25 wherein the solution is encapsulated in a hard gelatin capsule.

27. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of about 18% by weight of the total solution and (2) a total of about 0.5 molar equivalents (based on the compound (1)) of hydrochloric acid in a mixture of (a) propylene glycol in the amount of about 12% by weight of the total solution, (b) ethanol in the amount of from about 5% to about 6% by weight of the total solution, and (c) a saturated polyglycolized glyceride in the amount of from about 30% to about 35% by weight of the total solution.

28. The composition of claim 27 wherein the solution is encapsulated in a hard gelatin capsule.

29. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-

((5-thiazolyl)methoxycarbonyl)amino)-1,6-diphenyl-3-hydroxyhexane in the amount of about 22% by weight of the total solution and (2) a total of about 1.8 molar equivalents (based on the compound (1)) of hydrochloric acid in a mixture of (a) propylene glycol in the amount of about 20% by weight of the total solution, (b) ethanol in the amount of from about 5% to about 6% by weight of the total solution, and (c) a saturated polyglycolized glyceride in the amount of from about 30% to about 35% by weight of the total solution.

30. The composition of claim 29 wherein the solution is encapsulated in a hard gelatin capsule.

31. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of about 17% by weight of the total solution and (2) a total of about 0.4 molar equivalents (based on the compound (1)) of hydrochloric acid in a mixture of (a) propylene glycol in the amount of about 14% by weight of the total solution, (b) ethanol in the amount of about 12% by weight of the total solution, and (c) a saturated polyglycolized glyceride in the amount of from about 30% to about 35% by weight of the total solution.

32. The composition of claim 31 wherein the solution is encapsulated in a hard gelatin capsule.

33. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of from about 15% to about 20% by weight of the total solution and (2) a total of from about 0.2 to about 0.8 molar equivalents (based on the compound (1)) of hydrochloric acid in a mixture of (a) propylene glycol in the amount of from about 13% to about 14% by weight of the total solution, (b) ethanol in the amount of about 14% by weight of the total solution, and (c) a saturated polyglycolized glyceride in the amount of from about 30% to about 35% by weight of the total solution.

34. The composition of claim 33 wherein the solution is encapsulated in a hard gelatin capsule.

35. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of from about 10% to about 15% by weight of the total solution and (2) a total of from about 1.10 to about 1.30 molar equivalents (based on the compound (1)) of citric acid in a mixture of (a) propylene glycol in the amount of from about 5% to about 7% by weight of the total solution, (b) ethanol in the amount of from about 15% to about 20% by weight of the total solution, and (c) a saturated polyglycolized glyceride in the amount of from about 30% to about 35% by weight of the total solution.

36. The composition of claim 35 wherein the solution is encapsulated in a hard gelatin capsule.

37. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of from about 10% to about 15% by weight of the total solution and (2) a total of from about 0.8 to about 0.9 molar equivalents (based on the compound (1)) of citric acid in a mixture of (a) propylene glycol in the amount of from about 5% to about 7% by weight of the total solution, (b) ethanol in the amount of from about 10% to about 15% by weight of the total solution, (c) benzyl alcohol in the amount of from about 3% to about 4% by weight of the total solution, and (d) a saturated polyglycolized glyceride in the amount of from about 35% to about 40% by weight of the total solution.

38. The composition of claim 37 wherein the solution is encapsulated in a hard gelatin capsule.

39. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of about 20% by weight of the total solution and (2) a total of from about 0.7 to about 0.8 molar equivalents (based on the compound (1)) of citric acid in a mixture of (a) propylene glycol in the amount of from about 4% to about 6% by weight of the total solution, (b) ethanol in the amount of from about 10% to about 15% by weight of the total solution, (c) benzyl alcohol in the amount of from about 4% to about 6% by weight of the total solution, and (d) a saturated polyglycolized glyceride in the amount of from about 30% to about 35% by weight of the total solution.

40. The composition of claim 39 wherein the solution is encapsulated in a hard gelatin capsule.

41. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of about 25% by weight of the total solution and (2) a mixture of a total of from about 0.4 to about 0.5 molar equivalents (based on the compound (1)) of citric acid and from about 0.10 to about 0.25 molar equivalents (based on the compound (1)) of sulfuric acid in a mixture of (a) propylene glycol in the amount of from about 5% to about 7% by weight of the total solution, (b) ethanol in the amount of from about 10% to about 15% by weight of the total solution, (c) benzyl alcohol in the amount of from about 4% to about 6% by weight of the total solution, and (d) a saturated polyglycolized glyceride in the amount of from about 25% to about 30% by weight of the total solution.

42. The composition of claim 41 wherein the solution is encapsulated in a hard gelatin capsule.

43. The composition of claim 12 comprising a solution of: (1) (2S,3S,5S)-5-(N-(N-((N-Methyl-N-((2-isopropyl-4-thiazolyl)methyl)-amino)carbonyl)valinyl)-amino)-2-(N-((5-thiazolyl)methoxycarbonyl)amino)-1,6-diphenyl-3-hydroxyhexane in the amount of about 25% by weight of the total solution and (2) a total of from about 0.7 to about 0.8 molar equivalents (based on the compound (1)) of citric acid in a mixture of (a) propylene glycol in the amount of from about 4% to about 6% by weight of the total solution, (b) ethanol in the amount of from about 15% to about 20% by weight of the total solution, (c) benzyl alcohol in the amount of from about 5% to about 10% by weight of the total solution, and (d) a saturated polyglycolized glyceride in the amount of from about 25% to about 30% by weight of the total solution.

44. The composition of claim 43 wherein the solution is encapsulated in a hard gelatin capsule.

* * * * *

UNITED STATES PATENT AND TRADEMARK OFFICE
CERTIFICATE OF CORRECTION

PATENT NO. : 5,948,436
DATED : September 7, 1999
INVENTOR(S) : Laman A. Al-Razzak et al.

It is certified that error appears in the above-indentified patent and that said Letters Patent is hereby corrected as shown below:

Col. 23, line 41
 replace "Hydrochioric"
 with --Hydrochloric--.

Col. 24, line 20
 replace "5.13"
 with --5.10--.

Col. 26, line 25
 replace "prool"
 with --proof--.

Col. 26, line 7
 replace "reagenl"
 with --reagent--.

Col. 26, line 10
 replace "Iween"
 with --Tween--.

Col. 31, line 7
 replace "add"
 with --acid--.

Col. 31, line 9
 replace "Migyol"
 with --Miglyol--.

Col. 33, line 58
 replace "512"
 with --812--.

UNITED STATES PATENT AND TRADEMARK OFFICE
CERTIFICATE OF CORRECTION

PATENT NO. : 5,948,436
DATED : September 7, 1999
INVENTOR(S) : Laman A. Al-Razzak et al.

It is certified that error appears in the above-indentified patent and that said Letters Patent is hereby corrected as shown below:

Col. 37, line 31
 replace "5.o"
 with --5.0--.

Col. 38, line 54
 replace "adlibitum"
 with --ad libitum--.

Signed and Sealed this

Seventeenth Day of April, 2001

Attest:

NICHOLAS P. GODICI

*Attesting Officer*    Acting Director of the United States Patent and Trademark Office